(12) United States Patent
Sower et al.

(10) Patent No.: US 7,459,310 B2
(45) Date of Patent: Dec. 2, 2008

(54) CLONING AND EXPRESSION OF GONADOTROPIN-RELEASING HORMONE (GNRH) RECEPTORS

(75) Inventors: Stacia Sower, Newmarket, NH (US); Nathaniel V. Nucci, Philadelphia, PA (US); Matthew R. Silver, Dover, NH (US)

(73) Assignee: University of New Hampshire

( * ) Notice: Subject to any disclaimer, the term of this patent is extended or adjusted under 35 U.S.C. 154(b) by 402 days.

(21) Appl. No.: 11/103,082

(22) Filed: Apr. 11, 2005

(65) Prior Publication Data

US 2007/0231857 A1 Oct. 4, 2007

Related U.S. Application Data

(60) Provisional application No. 60/561,006, filed on Apr. 9, 2004.

(51) Int. Cl.
*C12N 5/10* (2006.01)
*C12N 15/12* (2006.01)
*C12N 15/63* (2006.01)
*C12N 1/21* (2006.01)

(52) U.S. Cl. .................... 435/325; 435/69.1; 435/252.3; 435/320.1; 536/23.5

(58) Field of Classification Search ........................ None
See application file for complete search history.

(56) References Cited

U.S. PATENT DOCUMENTS 5,985,583 A * 11/1999 Sealfon ....................... 435/7.2

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Skolnick et al. (2000). From genes to protein structure and function: novel applications of computational approaches in the genomic era. Trends in Biotechnology. 18:34-39.*
Sower et al. (2001). Molecular cloning of the GNRH receptor cDNA in the sea lamprey. Society for Neuroscience Abstracts. 27(2):1948.*
Norman, Anthony et al., Hormones Second Edition, 1997, p. 96, Academic Press, San Diego, CA.
Nozaki, Masumi, et al., The Distribution of Lamprey GnRH-III in Brains of Adult Sea Lampreys (*Petromyzon marinus*), General and Comparative Endocrinology, 2000, pp. 57-67, 118, Academic Press.
Sower, Stacia A., Evolution of GnRH in Fish of Ancient Organs, GnRH Neurons Gene to Behavior, 1997, pp. 27-49, Tokyo, Japan.
Sower, Stacia A., Brain and Pituitary Hormones of Lampreys, Recent Findings and their Evolutionary Significance, American Zoology, 1998, pp. 14-38, vol. 38.

Sower, Stacia A., Update: brain and pituitary hormones of lampreys, Comparative Biochemistry and Physiology Part B, 2001, pp. 291-302, vol. 129, Elsevier Science Inc.
Sower, Stacia A., Gonadotropin-Releasing Hormone in Primitive Fishes, Progress in Comparative Endocrinology, 1990, pp. 73-78, Wiley-Liss, Inc.
Knox, Christopher J., et al., Characterization and Localization of Gonadotropin-Releasing Hormone Receptors in the Adult Female Sea Lamprey, *Petromyzon marinus*, Endocrinology, 1994, pp. 492-498, vol. 134, No. 1, The Endocrine Society.
Matsuo, H., et al., Structure of the Porcine LH- and FSH-Releasing Hormone. I. The Proposed Amino Acid Sequence, Biochemical and Biophysical Research Communications, 1971, pp. 1334-1340, vol. 43, No. 6.
Burgus, Roger, et al., Primary Structure of the Ovine Hypothalamic Luteinizing Hormone-Releasing Factor (LRF), Proc. Nat. Acad. Sci. USA, Jan. 1972, pp. 278-282, vol. 69, No. 1.
Gupta, H.M., et al., A Novel Computer Modeling Approach to the Structures of Small Bioactive Peptides: The Structure of Gonadotropin-Releasing Hormone, Proteins: Structure, Function and Genetics, 1993, pp. 48-56.
Sealfon, S.C., et al. Molecular Mechanisms of Ligand Interaction with the Gonadotropin- Releasing Hormone Receptor, Endocrine Reviews, 1997, pp. 180-205, The Endocrine Society.
Sower, S.A., Goodman, et al., In Vivo Effects of Lamprey GnRH-I and Cyclized Analogs: A Structure- Activity Study, Neuropeptides, 1995, pp. 151-156, Pearson Professional Ltd.
Habibi, Hamid R., et al., Activity of Vertebrate Gonadotropin-Releasing Hormones and Analogs with Variant Amino Acid Residues in Positions 5, 7 and 8 in the Goldfish Pituitary, Regulatory Peptides, 1992, pp. 271-284, Elsevier Science Publishers B.V.

(Continued)

*Primary Examiner*—Christine J Saoud
*Assistant Examiner*—Jon M Lockard
(74) *Attorney, Agent, or Firm*—Devine, Millimet & Branch; Paul C. Remus; Raymond I. Bruttomesso, Jr.

(57) ABSTRACT

An isolated and purified GnRH protein receptor protein including an amino acid sequence selected from the group and an isolated and purified DNA which comprises a nucleotide sequence coding for the GnRH protein receptor protein. Also, a vector comprising the DNA of the GnRH protein receptor protein, a transformant carrying the vector comprising the DNA of the GnRH protein receptor protein, a process for producing a GnRH protein receptor protein or a salt thereof including culturing the transformant carrying the vector comprising the DNA of the GnRH protein receptor protein under sufficient conditions and for appropriate time to express the GnRH protein receptor protein, and a method of screening for a ligand to the GnRH protein receptor protein including contacting the GnRH protein receptor protein or a salt thereof with a sample to be tested. A screening method for a compound capable of inhibiting binding of the GnRH protein receptor protein with a ligand. Also, a kit for screening a compound capable of inhibiting binding of the GnRH protein receptor protein with a ligand including the GnRH protein receptor protein or a salt.

6 Claims, 9 Drawing Sheets

OTHER PUBLICATIONS

Pati, Debananda, et al., Inhibition of Human Hepatocarcinoma Cell Proliferation by Mammalian and Fish Gonadotropin-Releasing Hormones, Endocrinology, 1995, pp. 75-84, vol. 135, No. 1, The Endocrine Society.

Yu, Wen H., et al., A Hypothalamic Follicle-Stimulating Hormone-Releasing Decapeptide in the Rat, Proc. Natl. Acad. Sci. USA, Aug. 1997, pp. 9499-9503.

Dees, W.L., et al., Localization of Immunoreactive Lamprey Gonadotropin-Releasing Hormone in the Rat Brain, Peptides, 1999, pp. 1503-1511, Elsevier Science Inc.

Hiney, J.K., et al., Gonadotropin-Releasing Hormone Neurons in the Preoptic-Hypothalamic Region of the Rat Contain Lamprey Gonadotropin-Releasing Hormone III, Mammalian Luteinizing Hormone-Releasing Hormone, or Both Peptides, PNAS, Feb. 19, 2002, pp. 2386-2391, vol. 99, No. 4.

Tsutsumi, M., et al., Cloning and Functional Expression of a Mouse Gonadotrophin-Releasing Hormone Receptor, Molecular Endocrinology, 1992, pp. 1163-1169.

Kakar, S.S., et al., Cloning, Sequencing, and Expression of Human Gonadotropin-Releasing Hormone (GnRH) Receptor, Biochemical and Biophysical Research Communications, Nov. 30, 1992, pp. 289-295, vol. 189, No. 1, 1992, Academic Press, Inc.

Reinhart, J., et al., Molecular Cloning and Expression of cDNA Encoding the Murine Gonadotropin-Releasing Hormone Receptor, The Journal of Biological Chemistry, Oct. 25, 2002, pp. 21281-21284, vol. 267, No. 30.

Chi, L., et al., Cloning and Characterization of the Human GnRH Receptor, Molecular and Cellular Endocrinology, 1993, pp. R1-R6, vol. 91, Elsevier Scientific Publishers Ireland Ltd.

Perrin, M.H., et al., Molecular and Functional Characterization of GnRH Receptors Cloned from Rat Pituitary and a Mouse Pituitary Tumor Cell Line, Biochemical and Biophysical Research Communications, Mar. 31, 1993, pp. 1139-1144, vol. 191, No. 3, 1993, Academic Press, Inc.

Tensen, C., et al., Distinct Efficacies for Two Endogenous Ligands on a Single Cognate Gonadoliberin Receptor, Eur J Biochem, 1997, pp. 134-140.

Pawson, A.J., et al., Contrasting Internalization Kinetics of Human and Chicken Gonadotropin-Releasing Hormone Receptors Mediated by C-terminal Tail, Journal of Endocrinology, 1998, pp. R9-R12, vol. 156, Journal of Endocrinology Ltd., Great Britain.

Blomenrohr, M., et al., Pivotal Role for the Cytoplasmic Carboxyl-Terminal Tait of a Nonmammalian Gonadotropin-Releasing Hormone Receptor in Cell Surface Expression, Ligand Binding, and Receptor Phosphorylation and Internalization, Molecular Pharmacology, 1999, pp. 1229-1237, vol. 56, The American Society for Pharmacology and Experimental Therapeutics.

Lin, X., et al., Addition of Catfish Gonadotrophin-Releasing Hormone (GnRH) Receptor Intracellular Carboxyl-Terminal Tail to Rat GnRH Receptor Alters Receptor Expression and Regulation, Molecular Endocrinology, 1998, pp. 161-171, The Endocrine Society.

McArdle, C.A., et al., The Tail of the Gonadotropin-Releasing Hormone Receptor: Desensitization at, and Distal to, G Protein-Coupled Receptors, Molecular and Cellular Endocrinology, 1999, pp. 129-136, vol. 141, Elsevier Science Ireland Ltd.

McArdle, C.A., et al., Signalling, Cycling, and Desensitization of Gonadotropin-Releasing Hormone Receptors, Journal of Endocrinology, 2002, pp. 1-11, vol. 173, Society for Endocrinology, Great Britain.

Heding, A., et al., The Rat Gonadotropin-Releasing Hormone Receptor Internalizes via a β-Arrestin-Independent but Dynamin-Dependent, Pathway: Addition of a Carboxyl-Terminal Tail Confers β-Arrestin Dependency, Endocrinology, 2000, pp. 299-306, The Endocrine Society, United States.

Heding, A., et al., 1998. Gonadotropin-Releasing Hormone Receptors with Intracellular Carboxyl-Terminal Tails Undergo Acute Desensitization of Total Inositol Phosphate Production and Exhibit Accelerated Internalization Kinetics, The Journal of Biological Chemistry, 1998, pp. 11472-11477, vol. 273, No. 19, The American Society for Biochemistry and Molecular Biology, Inc., United States.

Hislop, J.N., et al., Differential Internalization of Mammalian and Non-Mammalian Gonadotropin-Releasing Hormone Receptors, Uncoupling of Dynamin-Dependent Internalization from Mitogen-Activated Protein Kinase Signaling, The Journal of Biological Chemistry, 2001, pp. 39685-39694, vol. 276, No. 43, The American Society for Biochemistry and Molecular Biology, Inc., United States.

Vrecl, M., et al., Internalization Kinetics of the Gonadotropin-Releasing Hormone (GnRH) Receptor, Pflugers Arch- Eur J Physiol, 2000, pp. R19-R20, vol. 439, Springer Veriag.

Willars, G.B., et al., Lack of a C-Terminal Tail in the Mammalian Gonadotropin-Releasing Hormone Receptor Confers Resistance to Agonist-Dependent Phosphorylation and Rapid Desensitization, The Journal of Biological Chemistry, 1999, pp. 30146-30153, vol. 274, No. 42, The American Society for Biochemistry and Molecular Biology, Inc., United States.

Troskie, B., et al., Identification of Three Putative GnRH Receptor Subtypes in Vertebrates, General and Comparative Endocrinology, 1998, pp. 296-302, vol. 112, Academic Press.

Reubi, J.C., et al., Specific Luteinizing-Hormone-Releasing Hormone Receptor Binding Sites in Hippocampus and Pituitary: An Autoradiographical Study, Neuroscience, 1987, pp. 847-856, vol. 21, No. 3, Pergamon Journals Ltd., Great Britain.

Morel, G., et al., Binding and Internalization of Native Gonadoliberin (GnRH) by Anterior Pituitary Gonadotrophs of the Rat, A Quantitative Autoradiographic Study After Cryoultramicrotomy, Cell Tissue Research, 1987, pp. 541-550, vol. 248, Springer Verlag.

Adams, T.E., et al., Gonadotropin-Releasing Hormone (GnRH) Receptor Dynamics and Gonadotrope Responsiveness During and After Continuous GnRH Stimulation, Biology of Reproduction, 1986, pp. 881-889, vol. 35.

Adams T.E., et al., Binding Characteristics of Gonadotropin-Releasing Hormone Receptors Throughout the Estrous Cycle of the Hamster, Endocrinology, 1981, pp. 2245-2253, vol. 108, No. 6, The Endocrine Society.

Clayton, R.N., et al., Luteinizing Hormone-Releasing Hormone Inactivation by Purified Pituitary Plasma Membranes: Effects of Receptor-Binding Studies, Endocrinology, 1979, pp. 1484-1494, The Endocrine Society.

Clayton, R.N., et al., Radioiodinated Nondegradable Gonadotropin-Releasing Hormone Analogs: New Probes for the Investigation of Pituitary Gonadotropin-Releasing Hormone Receptors, Endocrinology, 1979, pp. 1369-1376, vol. 104, No. 6, The Endocrine Society, United States.

Crowder, M.E., et al., Pituitary Content of Gonadotropins and Receptors for Gonadotropin-Releasing Hormone (GnRH) and Hypothalamic Content of GnRH During the Periovulatory Period of the Ewe, Endocrinology, 1984, pp. 234-239, vol. 114, No. 1, United States.

Habibi, H.R., et al., Characterization of Gonadotropin-Releasing Hormone (GnRH) Binding to Pituitary Receptors in Goldfish (Carassius auratus), Biology of Reproduction, 1987, pp. 844-853, vol. 36.

Habibi, H.R., et al. Photoaffinity Labeling of Pituitary Gonadotropin-Releasing Hormone Receptors in Goldfish (Carassius auratus), Biology of Reproduction, 1990, pp. 1006-1011, vol. 43.

Naik, S.I., et al., Pituitary Gonadotropin-Releasing Hormone Receptor Regulation in Mice. II: Females, Endocrinology, 1984, pp. 114-120, vol. 115, No. 1, The Endocrine Society, United States.

Pagelson, G. et al., Characterization of Gonadotropin-Releaasing Hormone Binding to Pituitary Receptors in the Gilthead Seabream (Sparus aurata), Biology of Reproduction, 1992, pp. 1004-1008, vol. 47.

Younglai, E.V., et al., The Pituitary Gonadotropin-Releasing Hormone (GnRH) Receptor of the Female Rabbit: Characterization and Developmental Aspects, Can J Physiol Pharmacol, 1992, pp. 1639-1646, vol. 70, Canada.

Hazum, E., et al., A Novel Method for Localization of Gonadotropin-Releasing Hormone Receptors, Endocrinology, 1982, pp. 2135-2137, vol. 111, No. 6, The Endocrine Society, United States.

Adams, T.E., et al., Gonadotropin-Releasing Hormone Receptor Binding and Pituitary Responsiveness in Estradiol-Primed Monkeys, Science, Sep. 18, 1981, pp. 1388-1391, vol. 213, AAAS.

Fraser, H.M., et al., GnRH Receptor mRNA Expression by In-Situ Hybridization in the Primate Pituitary and Ovary, Molecular Human Reproduction, 1996, pp. 117-121, vol. 2, No. 2, European Society for Human Reproduction and Embryology.

Byrne, B., et al., Isolation and Characterization of the Marmoset Gonadotropin-Releasing Hormone Receptor: Ser(140) of the DRS Motif is Substituted by Phe, Journal of Endocrinology, 1999, pp. 447-456, vol. 163, Society for Endocrinology, Great Britain.

Madigou, T., et al., Cloning, Tissue Distribution, and Central Expression of the Gonadotropin-Releasing Hormone Receptor in the Rainbow Trout (Oncorhynchus mykiss), Biology of Reproduction, 2000, pp. 1857-1866, vol. 63, the Society for the Study of Reproduction, Inc.

Illing, N., et al., Two Gonadotropin-Releasing Hormone Receptor Subtypes with Distinct Ligand Selectivity and Differential Distribution in Brain and Pituitary in the Goldfish (Carassius auratus), Physiology, Mar. 1999, pp. 2526-2531, vol. 96, Proceedings of the National Academy of Sciences, United States.

Bogerd, J., et al., Two Gonadotropin-Releasing Hormone Receptors in the African Catfish: No Differences in Ligand Selectivity, But Differences in Tissue Distribution, Endocrinology, 2002, pp. 4673-4682, vol. 143(12), The Endocrine Society, United States.

Okubo, K., et al., Identification and Characterization of Two Distinct GnRH Receptor Subtypes in a Teleost, the Medaka Oryzias Latipes, Endocrinology, 2001, pp. 4729-4739, The Endocrine Society, United States.

Neill J.D., et al., A Gonadotropin-Releasing Hormone (GnRH) Receptor Specific for GnRH II in Primates, Biochemical and Biophysical Research Communications, 2001, pp. 1012-1018, vol. 282, Academic Press.

Millar, R., et al., A Novel Mammalian Receptor for the Evolutionarily Conserved Type II GnRH, Proceedings of the National Academy of Sciences, Aug. 14, 2001, pp. 9636-9641, vol. 98, No. 17.

Seong, J.Y., et al., Ala/Thr$^{201}$ in Extracellular Loop 2 and Leu/Phe$^{290}$ in Transmembrane Domain 6 in Type I Frog Gonadotropin-releasing Hormone Receptor Confer Differential Ligand Sensitivity and Signal Transduction, Endocrinology, 2003, pp. 454-466, vol. 144, The Endocrine Society, United States.

Wang, L., et al., Three Distinct Types of GnRH Receptor Characterized in the Bullfrog, Proceedings of the National Academy of Sciences, Jan. 2, 2001, pp. 361-366, vol. 98, No. 1.

Sherwood, N.M., et al., Primary Structure of Gonadotropin-Releasing Hormone from Lamprey Brain, The Journal of Biological Chemistry, Apr. 15, 1986, pp. 4812-4819, vol. 261, No. 11., United States.

Sower, S.A., et al., Primary Structure and Biological Activity of a Third Gonadotropin-Releasing Hormone from Lamprey Brain, Endocrinology, 1993, pp. 1225-1231, vol. 132, No. 3, The Endocrine Society, United States.

Bolduc, T.G., et al., Changes in Brain Gonadotropin-Releasing Hormone, Plasma Estradiol 17-β, and Progesterone During the Final Reproductive Cycle of the Female Sea Lapmrey, Petromyzon marinus, The Journal of Experimental Zoology, 1992, pp. 55-63, vol. 264, Wiley-Liss, Inc.

Deragon K.L., et al., Effects of Lamprey Gonadotropin-Releasing Hormone-III on Steroidgenesis and Spermiation in Male Sea Lampreys, General and Comparative Endocrinology, 1994, pp. 363-367, Academic Press.

Fahien, C.M., et al., Relationship Between Brain Gonadotropin-Releasing Hormone and Final Reproductive Period of the Adult Male Sea Lamprey, Petromyzon marinus, General and Comparative Endocrinology, 1990, pp. 427-437, vol. 80, Academic Press.

Gazourian, L., et al., Characteristics of GnRH Binding in the Gonads and Effects of Lamprey GnRH-I and -III on Reproduction in the Adult Sea Lamprey, General and Comparative Endocrinology, 1997, pp. 327-339, vol. 108, Academic Press.

King, J.C., et al., Neuronal Systems Immunoreactive with Antiserum to Lamprey Gonadotropin-Releasing Hormone in the Brain of Petromyzon marinus, Cell and Tissue Research, 1988, pp. 1-8, vol. 253, Springer-Verlag.

Materne, O.L., et al., Characterization of the Gonadotropin-Releasing Hormone Binding Sites in the Pituitary and Gonads of the Sexually Maturing Adult Lamprey, XIII International Congress of Comparative Endocrinology, Nov. 16-21, 1997, Monduzzi Editore S.p.A., Bologna, Italy.

Nozaki, M., et al., Diffusion Between the Neurohypophysis and the Adenohypophysis of Lampreys, Petromyzon marinus, General and Comparative Endocrinology, 1994, pp. 385-391, vol. 95, Academic Press, Inc.

Nozaki, M., et al., Possible Gonadotropin Cells in the Lamprey Pituitary: Colocalization of Mammalian LH-Like Immunoreactivity and Glycoconjugate in Adult Sea Lampreys (Petromyzon marinus), General and Comparative Endocrinology, 1999, pp. 23-31, vol. 113, Academic Press.

Root, A.R., et al., In Situ Chracterization of Gonadotropin-Releasing Hormine-I, -III, and Glutamic Acid Decarboxylase Expression in the Brain of the Sea Lamprey, Petromyzon marinus, Brain, Behavior and Evolution, Oct. 6, 2004, pp. 60-70, vol. 65, S. Karger AG, Basel.

Sower, S.A., et al., In Vivo Effects of Lamprey GnRH-I and Cyclized Analogs: A Structure-Activity Study, Neuropeptides, pp. 151-156, vol. 29, Pearson Professional Ltd., 1995.

Sower, S.A., et al., Evidence for Lamprey GnRH-I and -III-Like Molecules in the Brains of the Southern Hemisphere Lampreys Geotria australis and Modacia mordax, General and Comparative Endocrinology, 2000, pp. 168-175, vol. 120, Academic Press.

Suzuki, K, et al., Multiple Transcripts Encoding Lamprey Gonadotropin-Releasing Hormone-I Precursors, Journal of Molecular Endocrinology, 2000, pp. 365-376, vol. 24, Society for Endocrinology, Great Britain.

Tobet, S.A., et al., Distribution of Lamprey Gonadotropin-Releasing Hormone-III in Brains of Larval Lampreys (Peteromyzon marinus), Cell & Tissue Research, 1995, pp. 261-270, vol. 279, Springer-Verlag.

Tobet, S.A., et al., Relationship of Gonadotropin-Releasing Hormone (GnRH) Neurons to the Olfactory System in the Developing Lamprey (Petromyzon marinus), The Journal of Comparative Neurology, 1996, pp. 97-111, vol. 376, Wiley-Liss, Inc.

Wright, G.M., et al., Distribution of Lamprey Gonadotropin-Releasing Hormone in the Brain and Pituitary Gland of Larval, Metamorphic, and Adult Sea Lampreys, Petromyzon marinus. Can J Zool, 1994, pp. 48-53, vol. 72.

Youson, J.H., et al., Concentration of Gonadotropin-Releasing Hormones in Brain of Larval and Metamorphosing Lampreys of Two Species with Different Adult Life Histories. Fifth International Symposium on Reproductive Physiology of Fish, Austin, TX, 1995, p. 83.

Youson, J.H., et al., Concentration of Gonadotropin-Releasing Hormone in the Brain During Metamorphosis in the Lamprey, Petromyzon marinus, The Journal of Experimental Zoology, 1991, pp. 399-404, vol. 259, Wiley-Liss, Inc.

Alok D., et al., 2000. Characterization of a Pituitary GnRH-Receptor from a Perciform Fish, Morone saxatilis: Functional Expression in a Fish Cell Line, Molcular and Cellular Endocrinology, 2000, pp. 65-75, vol. 168, Elsevier Science Ireland Ltd.

Sambrook, J., et al., Molecular Cloning: A Laboratory Manual, Third Edition, 2001, vol. 1, Cold Spring Harbor Laboratory Press, Cold Spring Harbor, NY.

Sun, Y.M., et al., A Chicken Gonadotropin-Releasing Hormone Receptor that Confers Agonist Activity to Mammalian Antagonists. Identification of $_D$-Lys$^6$ in the Ligand and Extracellular Loop Two of the Receptor as Determinants, The Journal of Biological Chemistry, Mar. 16, 2001, pp. 7754-7761, vol. 276, No. 11, The American Society for Biochemistry and Molecular Biology, Inc., United States.

Swofford, D.L., PAUP* Phylogenetic Analysis Using Parsimony (*and Other Methods), Version 4.0 beta version, Feb. 2002, Sinauer Associates, Sunderland, Massachusetts.

Eidne K.A., et al., Molecular Cloning and Characterization of the Rat Pituitary Gonadotropin-Releasing Hormone (GnRH) Receptor, Molecular and Cellular Endocrinology, 1992, pp. R5-R9, vol. 90, Elsevier Scientific Publishers Ireland, Ltd.

Kaiser, U.B., et al., Isolation and Characterization of cDNA's Encoding in the Rat Pituitary Gonadotropin-Releasing Hormone Receptor, Biochemical and Biophysical Research Communications, Dec. 30, 1992, pp. 1645-1652, vol. 189, No. 3, Academic Press, Inc.

Kudo, A., et al., Isolation of Rat GnRH Receptor cDNA Having Different 5'-Noncoding Sequence, Zoological Science, 1993, pp. 863-867, vol. 10, Zoological Society of Japan.

Campion, C.E., et al., The Gene Encoding the Ovine Gonadotropin-Releasing Hormone (GnRH) Receptor: Cloning and Initial Characterization, Gene, 1996, pp. 277-280, vol. 170, Elsevier Science B.V.

Kakar, S.S., te al., Molecular Cloning, Sequencing, and Characterizing the Bovine Receptor for Gonadotropin-Releasing Hormone (GnRH), Domestic Animal Endocrinology, 1993, pp. 335-342, vol. 10(4), Butterworth-Heinemann.

Weesner, G.D., et al., Rapid Communication: Nucleotide Sequence of Luteinizing Hormone-Releasing Hormone (LHRH) Receptor cDNA in the Pig Pituitary, Journal of Animal Science, 1994, p. 1911, vol. 72.

Santra, S., et al., Cloning and Characterization of Bonnet Monkey GnRH Recepto, Molecular Human Reproduction, 2000, pp. 415-421, vol. 6, No. 5, European Society of Human Reproduction and Embryology.

Cui, J., et al., Identification of Phe[313] of the Gonadotropin-Releasing Hormone (GnRH) Receptor as a Site Critical for the Binding of Nonpeptide GnRH Antagonists, Molecular Endocrinology, 2000, pp. 671-681, vol. 14(5), The Endocrine Society, USA.

Cheung, T.C., et al. Molecular Cloning and Tissue Expression of the Gonadotropin-Releasing Hormone Receptor in the Tammar Wallaby (*Macropus eugenii*), Reproductive Fertility Development, 2002, pp. 157-164, vol. 14, CSIRO.

Hauser, F., et al., Molecular Cloning, Genomic Organization and Developmental Regulation of a Novel Receptor from *Drosophila melanogaster* Structurally Related to Gonadotropin-Releasing Hormone Receptors for Vertebrates, Biochemical and Biophysical Research Communications, 1998, pp. 822-828, vol. 249, Academic Press.

Okubu, K., et al., Molecular Cloning and Tissue-Specific Expression of a Gonadotropin-Releasing Hormone Receptor in the Japanese Eel, General and Comparative Endocrinology, 2000, pp. 181-192, vol. 119, Academic Press.

Jimenez-Linan, M., et al., Examination of Guinea Pig Luteinizing Hormone-Releasing Hormone Gene Reveals a Unique Decapeptide and Existence of Two Transcripts in the Brain, Endocrinology, 1997, pp. 4123-4130, vol. 138., No. 10, The Endocrine Society, U.S.A.

* cited by examiner

SEQUENCE LISTING

```
<160> NUMBER OF SEQ ID NOS: 42

<210> SEQ ID NO 1
<211> LENGTH: 1838
<212> TYPE: DNA
<213> ORGANISM: Petromyzon marinus
<220> FEATURE:
<221> NAME/KEY: CDS
<222> LOCATION: (55)..(1434)

<400> SEQUENCE: 1
ttgttgcagt gcccaggacc gagtcatccg tgtgatggag atttgtccca tcct atg      57
                                                              Met
                                                                1
```

-continued

| | |
|---|---|
| aag tgc gct ttg atg gaa ccc atc aac atg aac atg aca ccc cgg gcc<br>Lys Cys Ala Leu Met Glu Pro Ile Asn Met Asn Met Thr Pro Arg Ala<br>           5                        10                    15 | 105 |
| gcc ttc ctc aac aac gtg acg ggc cct ccg aac gcc agc cac aca ggc<br>Ala Phe Leu Asn Asn Val Thr Gly Pro Pro Asn Ala Ser His Thr Gly<br>          20                      25                       30 | 153 |
| gac gag caa ctc acc aac tcc agc atc aac tcc gac atc cgg ttg cca<br>Asp Glu Gln Leu Thr Asn Ser Ser Ile Asn Ser Asp Ile Arg Leu Pro<br>       35                      40                    45 | 201 |
| gcc acg cag ttc cgt gtc atc agc acc ttt gcc ctc ttc atc ttc gcg<br>Ala Thr Gln Phe Arg Val Ile Ser Thr Phe Ala Leu Phe Ile Phe Ala<br>50                   55                      60                  65 | 249 |
| gcc ata agc aac ttg acc gtg ttg tgc acc atc tcc cac aac cac cgc<br>Ala Ile Ser Asn Leu Thr Val Leu Cys Thr Ile Ser His Asn His Arg<br>               70                      75                    80 | 297 |
| aag acc aag tcg cac gtg cgc atc ctc atc gtg aac ctg acg acg gcc<br>Lys Thr Lys Ser His Val Arg Ile Leu Ile Val Asn Leu Thr Thr Ala<br>       85                      90                    95 | 345 |
| gac ctg ctc atc aca ttc atc gtg atg ccc ctg gac gcc gtg tgg cac<br>Asp Leu Leu Ile Thr Phe Ile Val Met Pro Leu Asp Ala Val Trp His<br>100                   105                    110 | 393 |
| atc acg acg cag tgg tac gcg ggc gag ttc gcc tgc cgc ctc ctc atg<br>Ile Thr Thr Gln Trp Tyr Ala Gly Glu Phe Ala Cys Arg Leu Leu Met<br>115                   120                    125 | 441 |
| ttc ctg cgc ctc ctc gcc atg tac tcc agc gcc ttc atc acc gtg gtc<br>Phe Leu Arg Leu Leu Ala Met Tyr Ser Ser Ala Phe Ile Thr Val Val<br>130                   135                    140                    145 | 489 |
| atc agc ttg gac cgc cac tcg gcc atc ctc aat ccg ctg ggc atc ggc<br>Ile Ser Leu Asp Arg His Ser Ala Ile Leu Asn Pro Leu Gly Ile Gly<br>                   150                    155                    160 | 537 |
| aaa gcc aag gcc aaa aac aag acc atg ctg agc gtg gcc tgg gtc ctc<br>Lys Ala Lys Ala Lys Asn Lys Thr Met Leu Ser Val Ala Trp Val Leu<br>165                   170                    175 | 585 |
| agc gtt ctg ctg gcg gtc ccg cag ctc ttt ctg ttc cac gta aag agt<br>Ser Val Leu Leu Ala Val Pro Gln Leu Phe Leu Phe His Val Lys Ser<br>180                   185                    190 | 633 |
| ccc aaa gga aac aaa aac ttc gtt cag tgc gtc acc cac ggc aac ttc<br>Pro Lys Gly Asn Lys Asn Phe Val Gln Cys Val Thr His Gly Asn Phe<br>195                   200                    205 | 681 |
| gtc gag cag tgg cac cac aat ctc tac tac atg ttc acg ttc gtg ttc<br>Val Glu Gln Trp His His Asn Leu Tyr Tyr Met Phe Thr Phe Val Phe<br>210                   215                    220                    225 | 729 |
| ctc ttc ata ctg cca ctc ttc att atg ata ttc tgc tac tgc cgg att<br>Leu Phe Ile Leu Pro Leu Phe Ile Met Ile Phe Cys Tyr Cys Arg Ile<br>                   230                    235                    240 | 777 |
| ttg ctg gag atc tcc aag agg atg cga gaa gga agc att tcg tcc aaa<br>Leu Leu Glu Ile Ser Lys Arg Met Arg Glu Gly Ser Ile Ser Ser Lys<br>245                   250                    255 | 825 |
| gag atc cgc ctt cgc cgc tca aac aac aac atc ccc aag gcc cgc atg<br>Glu Ile Arg Leu Arg Arg Ser Asn Asn Asn Ile Pro Lys Ala Arg Met<br>260                   265                    270 | 873 |
| cgc acc ctc aag atg agc atc gcc atc gtc agc tcc ttc gtg gtc tgc<br>Arg Thr Leu Lys Met Ser Ile Ala Ile Val Ser Ser Phe Val Val Cys<br>275                   280                    285 | 921 |
| tgg acg ccc tac tac gtc ctc ggc atc tgg tac tgg ttc gac cgg agc<br>Trp Thr Pro Tyr Tyr Val Leu Gly Ile Trp Tyr Trp Phe Asp Arg Ser<br>290                   295                    300                    305 | 969 |
| att gtg tca cgc aag gtc gtg ccg cac ttc gtc gag gag atg tcc ctg<br>Ile Val Ser Arg Lys Val Val Pro His Phe Val Glu Glu Met Ser Leu | 1017 |

-continued

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 310 |     |     |     |     | 315 |     |     |     |     | 320 |     |     |     |      |
| acg | ttc | ggg | ctg | ctg | aac | gcg | tgc | ctg | gac | ccc | gtc | atc | tac | ggc | gtg | 1065 |
| Thr | Phe | Gly | Leu | Leu | Asn | Ala | Cys | Leu | Asp | Pro | Val | Ile | Tyr | Gly | Val |      |
|     |     | 325 |     |     |     |     | 330 |     |     |     |     | 335 |     |     |     |      |
| ttc | gcg | gcg | cac | gtt | cgc | cgc | gag | gtg | cgc | cgc | tgc | tgc | cgc | tgg | ccc | 1113 |
| Phe | Ala | Ala | His | Val | Arg | Arg | Glu | Val | Arg | Arg | Cys | Cys | Arg | Trp | Pro |      |
|     |     | 340 |     |     |     |     | 345 |     |     |     |     | 350 |     |     |     |      |
| cgg | act | gcg | gcg | cat | gac | aga | gac | tcg | tca | tcc | acg | ccc | gtc | acg | ggc | 1161 |
| Arg | Thr | Ala | Ala | His | Asp | Arg | Asp | Ser | Ser | Ser | Thr | Pro | Val | Thr | Gly |      |
|     |     | 355 |     |     |     |     | 360 |     |     |     |     | 365 |     |     |     |      |
| tcc | ttt | cgc | tac | tcg | gcc | tcg | tcc | gtg | cgg | agt | cgc | cgg | gtg | ccc | ttc | 1209 |
| Ser | Phe | Arg | Tyr | Ser | Ala | Ser | Ser | Val | Arg | Ser | Arg | Arg | Val | Pro | Phe |      |
| 370 |     |     |     |     | 375 |     |     |     |     | 380 |     |     |     |     | 385 |      |
| gcg | tgc | ggg | gag | cag | ccc | gag | gcc | acc | ggc | gcg | cac | ccc | aca | ccc | gcc | 1257 |
| Ala | Cys | Gly | Glu | Gln | Pro | Glu | Ala | Thr | Gly | Ala | His | Pro | Thr | Pro | Ala |      |
|     |     |     |     | 390 |     |     |     |     | 395 |     |     |     |     | 400 |     |      |
| acg | agg | ctg | ctg | cag | agg | ggc | tgc | tta | gtc | gcg | ggg | gtc | ccc | gtg | aac | 1305 |
| Thr | Arg | Leu | Leu | Gln | Arg | Gly | Cys | Leu | Val | Ala | Gly | Val | Pro | Val | Asn |      |
|     |     |     |     | 405 |     |     |     |     | 410 |     |     |     |     | 415 |     |      |
| aga | gcg | gca | gcc | ggg | atg | gcc | gct | ggt | gcg | aag | gcg | ttc | tgt | gat | gcc | 1353 |
| Arg | Ala | Ala | Ala | Gly | Met | Ala | Ala | Gly | Ala | Lys | Ala | Phe | Cys | Asp | Ala |      |
|     |     |     |     | 420 |     |     |     |     | 425 |     |     |     |     | 430 |     |      |
| agt | ggt | ggt | ggc | gct | ggt | ggt | ggc | gga | gga | gga | ggc | gaa | ggg | tgc | act | 1401 |
| Ser | Gly | Gly | Gly | Ala | Gly | Gly | Gly | Gly | Gly | Gly | Gly | Glu | Gly | Cys | Thr |      |
|     |     |     |     | 435 |     |     |     |     | 440 |     |     |     |     | 445 |     |      |
| gag | aaa | act | ctc | gta | tgt | cct | gaa | agc | tgc | atc | tgcatgggtg gtggtggtgg |   |   |   | 1454 |
| Glu | Lys | Thr | Leu | Val | Cys | Pro | Glu | Ser | Cys | Ile |     |     |     |     |     |      |
| 450 |     |     |     |     | 455 |     |     |     |     | 460 |     |     |     |     |     |      | tgtggtgcct attagaagtg tgtgtgtgtg tttgcgatag ttaatttcgt gagaacgcac 1514 gatgggtttg aaagtttgag ttcatggcca ctacttgcgt agttgtgtat gtaatctgtg 1574 ggtagcattc ctcccttag tgagcttcgt tattgttttc tagtgagaat aacgcacgac 1634 actgcgagtt aaaaatatat ttatggaagc tgtatgttag taatttatag ttatgtttta 1694 ttgcactgtg tatgccttga caccatacgt aaatatatta caaatatttt tcttaatgtg 1754 tttccatgca cagcatacag tataataaaa aaaacattac aaataaatgt gatatctaag 1814 atattacatt atatgaaatc aaaa 1838

<210> SEQ ID NO 2
<211> LENGTH: 460
<212> TYPE: PRT
<213> ORGANISM: Petromyzon marinus

<400> SEQUENCE: 2

Met Lys Cys Ala Leu Met Glu Pro Ile Asn Met Asn Met Thr Pro Arg
1               5                   10                  15

Ala Ala Phe Leu Asn Asn Val Thr Gly Pro Pro Asn Ala Ser His Thr
            20                  25                  30

Gly Asp Glu Gln Leu Thr Asn Ser Ser Ile Asn Ser Asp Ile Arg Leu
        35                  40                  45

Pro Ala Thr Gln Phe Arg Val Ile Ser Thr Phe Ala Leu Phe Ile Phe
    50                  55                  60

Ala Ala Ile Ser Asn Leu Thr Val Leu Cys Thr Ile Ser His Asn His
65                  70                  75                  80

Arg Lys Thr Lys Ser His Val Arg Ile Leu Ile Val Asn Leu Thr Thr
                85                  90                  95

Ala Asp Leu Leu Ile Thr Phe Ile Val Met Pro Leu Asp Ala Val Trp

```
                    100                 105                 110
His Ile Thr Thr Gln Trp Tyr Ala Gly Glu Phe Ala Cys Arg Leu Leu
            115                 120                 125

Met Phe Leu Arg Leu Leu Ala Met Tyr Ser Ser Ala Phe Ile Thr Val
        130                 135                 140

Val Ile Ser Leu Asp Arg His Ser Ala Ile Leu Asn Pro Leu Gly Ile
145                 150                 155                 160

Gly Lys Ala Lys Ala Lys Asn Lys Thr Met Leu Ser Val Ala Trp Val
                165                 170                 175

Leu Ser Val Leu Leu Ala Val Pro Gln Leu Phe Leu Phe His Val Lys
            180                 185                 190

Ser Pro Lys Gly Asn Lys Asn Phe Val Gln Cys Val Thr His Gly Asn
        195                 200                 205

Phe Val Glu Gln Trp His His Asn Leu Tyr Tyr Met Phe Thr Phe Val
            210                 215                 220

Phe Leu Phe Ile Leu Pro Leu Phe Ile Met Ile Phe Cys Tyr Cys Arg
225                 230                 235                 240

Ile Leu Leu Glu Ile Ser Lys Arg Met Arg Glu Gly Ser Ile Ser Ser
                245                 250                 255

Lys Glu Ile Arg Leu Arg Arg Ser Asn Asn Asn Ile Pro Lys Ala Arg
            260                 265                 270

Met Arg Thr Leu Lys Met Ser Ile Ala Ile Val Ser Ser Phe Val Val
        275                 280                 285

Cys Trp Thr Pro Tyr Tyr Val Leu Gly Ile Trp Tyr Trp Phe Asp Arg
        290                 295                 300

Ser Ile Val Ser Arg Lys Val Val Pro His Phe Val Glu Glu Met Ser
305                 310                 315                 320

Leu Thr Phe Gly Leu Leu Asn Ala Cys Leu Asp Pro Val Ile Tyr Gly
                325                 330                 335

Val Phe Ala Ala His Val Arg Arg Glu Val Arg Arg Cys Cys Arg Trp
            340                 345                 350

Pro Arg Thr Ala Ala His Asp Arg Asp Ser Ser Ser Thr Pro Val Thr
        355                 360                 365

Gly Ser Phe Arg Tyr Ser Ala Ser Ser Val Arg Ser Arg Arg Val Pro
    370                 375                 380

Phe Ala Cys Gly Glu Gln Pro Glu Ala Thr Gly Ala His Pro Thr Pro
385                 390                 395                 400

Ala Thr Arg Leu Leu Gln Arg Gly Cys Leu Val Ala Gly Val Pro Val
                405                 410                 415

Asn Arg Ala Ala Ala Gly Met Ala Ala Gly Ala Lys Ala Phe Cys Asp
            420                 425                 430

Ala Ser Gly Gly Gly Ala Gly Gly Gly Gly Gly Gly Glu Gly Cys
        435                 440                 445

Thr Glu Lys Thr Leu Val Cys Pro Glu Ser Cys Ile
    450                 455                 460

<210> SEQ ID NO 3
<211> LENGTH: 25
<212> TYPE: DNA
<213> ORGANISM: Artificial sequence
<220> FEATURE:
<223> OTHER INFORMATION: Description of Artificial Sequence: Synthetic
      Degenerate primer
<220> FEATURE:
<221> NAME/KEY: modified_base
<222> LOCATION: (12)..(12)
```

```
<223> OTHER INFORMATION: n is a, c, g, or t

<400> SEQUENCE: 3
ctcgaattcg gnathtggta ytggt                                          25

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      Degenerate primer
<220> FEATURE:
<221> NAME/KEY: modified_base
<222> LOCATION: (16)..(16)
<223> OTHER INFORMATION: n is a, c, g, or t
<220> FEATURE:
<221> NAME/KEY: modified_base
<222> LOCATION: (19)..(19)
<223> OTHER INFORMATION: n is a, c, g, or t

<400> SEQUENCE: 4
acactcgagc crtadntrng grtc                                           24

<210> SEQ ID NO 5
<211> LENGTH: 27
<212> TYPE: DNA
<213> ORGANISM: Artificial sequence
<220> FEATURE:
<223> OTHER INFORMATION: Description of Artificial Sequence: Synthetic
      Universal primer

<400> SEQUENCE: 5
aactggaaga attcgcggcc gcaggaa                                        27

<210> SEQ ID NO 6
<211> LENGTH: 18
<212> TYPE: DNA
<213> ORGANISM: Artificial sequence
<220> FEATURE:
<223> OTHER INFORMATION: Description of Artificial Sequence: Synthetic
      poly T sequence

<400> SEQUENCE: 6
tttttttttt tttttttt                                                  18

<210> SEQ ID NO 7
<211> LENGTH: 25
<212> TYPE: DNA
<213> ORGANISM: Petromyzon marinus

<400> SEQUENCE: 7
cggagcattg tgtcacgcaa ggtcg                                          25

<210> SEQ ID NO 8
<211> LENGTH: 25
<212> TYPE: DNA
<213> ORGANISM: Petromyzon marinus

<400> SEQUENCE: 8
cgaccttgcg tgacacaatg ctccg                                          25

<210> SEQ ID NO 9
<211> LENGTH: 25
<212> TYPE: DNA
<213> ORGANISM: Petromyzon marinus
```

<400> SEQUENCE: 9
atccgtgtga tggagatttg tgcca                                    25

<210> SEQ ID NO 10
<211> LENGTH: 25
<212> TYPE: DNA
<213> ORGANISM: Petromyzon marinus

<400> SEQUENCE: 10
tggcacaaat ctccatcaca cggat                                    25

<210> SEQ ID NO 11
<211> LENGTH: 21
<212> TYPE: DNA
<213> ORGANISM: Petromyzon marinus

<400> SEQUENCE: 11
ccgaacgcca gccacacagg c                                        21

<210> SEQ ID NO 12
<211> LENGTH: 21
<212> TYPE: DNA
<213> ORGANISM: Petromyzon marinus

<400> SEQUENCE: 12
gcctgtgtgg ctggcgttcg g                                        21

<210> SEQ ID NO 13
<211> LENGTH: 20
<212> TYPE: DNA
<213> ORGANISM: Petromyzon marinus

<400> SEQUENCE: 13
gcgggcgagt tcgtctgccg                                          20

<210> SEQ ID NO 14
<211> LENGTH: 20
<212> TYPE: DNA
<213> ORGANISM: Petromyzon marinus

<400> SEQUENCE: 14
cggcagacga actcgcccgc                                          20

<210> SEQ ID NO 15
<211> LENGTH: 25
<212> TYPE: DNA
<213> ORGANISM: Petromyzon marinus

<400> SEQUENCE: 15
ggctcggctc aaagtgaatc cgctg                                    25

<210> SEQ ID NO 16
<211> LENGTH: 25
<212> TYPE: DNA
<213> ORGANISM: Petromyzon marinus

<400> SEQUENCE: 16
cagcggattc actttgagcc gagcc                                    25

<210> SEQ ID NO 17
<211> LENGTH: 20
<212> TYPE: DNA
<213> ORGANISM: Petromyzon marinus

<400> SEQUENCE: 17
agcgttctgc tggcggtccc                    20

<210> SEQ ID NO 18
<211> LENGTH: 26
<212> TYPE: DNA
<213> ORGANISM: Petromyzon marinus

<400> SEQUENCE: 18
tcacccacgg caacttcgtc gagcag             26

<210> SEQ ID NO 19
<211> LENGTH: 24
<212> TYPE: DNA
<213> ORGANISM: Petromyzon marinus

<400> SEQUENCE: 19
gcccctccga acgccagcca caca                24

<210> SEQ ID NO 20
<211> LENGTH: 21
<212> TYPE: DNA
<213> ORGANISM: Petromyzon marinus

<400> SEQUENCE: 20
gcccctggac gccgtgtggc a                   21

<210> SEQ ID NO 21
<211> LENGTH: 24
<212> TYPE: DNA
<213> ORGANISM: Petromyzon marinus

<400> SEQUENCE: 21
cggtcccgca gctctttctg ttcc                24

<210> SEQ ID NO 22
<211> LENGTH: 29
<212> TYPE: DNA
<213> ORGANISM: Petromyzon marinus

<400> SEQUENCE: 22
caaaaacttc gttcagtgcg tcacccacg           29

<210> SEQ ID NO 23
<211> LENGTH: 33
<212> TYPE: DNA
<213> ORGANISM: Petromyzon marinus

<400> SEQUENCE: 23
tggtattggt tcgaccggag cattgtgtca cgc      33

<210> SEQ ID NO 24
<211> LENGTH: 25
<212> TYPE: DNA
<213> ORGANISM: Petromyzon marinus

<400> SEQUENCE: 24
aacttgaccg tgttgtgcac catct               25

<210> SEQ ID NO 25
<211> LENGTH: 25
<212> TYPE: DNA

```
<213> ORGANISM: Petromyzon marinus

<400> SEQUENCE: 25
gatctccaag aggatgcgag aagga                                          25

<210> SEQ ID NO 26
<211> LENGTH: 25
<212> TYPE: DNA
<213> ORGANISM: Petromyzon marinus

<400> SEQUENCE: 26
caaaaacttc gttcagtgcg tcacc                                          25

<210> SEQ ID NO 27
<211> LENGTH: 25
<212> TYPE: DNA
<213> ORGANISM: Petromyzon marinus

<400> SEQUENCE: 27
tctccaagag gatgcgagaa ggaag                                          25

<210> SEQ ID NO 28
<211> LENGTH: 25
<212> TYPE: DNA
<213> ORGANISM: Petromyzon marinus

<400> SEQUENCE: 28
caagaggatg cgagaaggaa gcatt                                          25

<210> SEQ ID NO 29
<211> LENGTH: 22
<212> TYPE: DNA
<213> ORGANISM: Petromyzon marinus

<400> SEQUENCE: 29
ccaccactgg catcacagaa cg                                             22

<210> SEQ ID NO 30
<211> LENGTH: 22
<212> TYPE: DNA
<213> ORGANISM: Petromyzon marinus

<400> SEQUENCE: 30
gaggccgagt agcgaaagga gc                                             22

<210> SEQ ID NO 31
<211> LENGTH: 18
<212> TYPE: DNA
<213> ORGANISM: Petromyzon marinus

<400> SEQUENCE: 31
gccgctgctg ccgctggc                                                  18

<210> SEQ ID NO 32
<211> LENGTH: 24
<212> TYPE: DNA
<213> ORGANISM: Petromyzon marinus

<400> SEQUENCE: 32
cgtcacgggc tcctttcgct actc                                           24

<210> SEQ ID NO 33
<211> LENGTH: 24
```

-continued

```
<210> SEQ ID NO 33
<211> LENGTH: 24
<212> TYPE: DNA
<213> ORGANISM: Petromyzon marinus

<400> SEQUENCE: 33
cacgggctcc tttcgctact cggc                                            24

<210> SEQ ID NO 34
<211> LENGTH: 22
<212> TYPE: DNA
<213> ORGANISM: Petromyzon marinus

<400> SEQUENCE: 34
cgcagtgtct gcgttattct ca                                              22

<210> SEQ ID NO 35
<211> LENGTH: 26
<212> TYPE: DNA
<213> ORGANISM: Artificial Sequence
<220> FEATURE:
<223> OTHER INFORMATION: Description of Artificial Sequence: Synthetic
      Degenerate primer
<220> FEATURE:
<221> NAME/KEY: modified_base
<222> LOCATION: (18)
<223> OTHER INFORMATION: n is a, c, g, or t
<220> FEATURE:
<221> NAME/KEY: modified_base
<222> LOCATION: (21)
<223> OTHER INFORMATION: n is a, c, g, or t

<400> SEQUENCE: 35
acactcgagc crtadatntr nggrtc                                          26

<210> SEQ ID NO 36
<211> LENGTH: 410
<212> TYPE: PRT
<213> ORGANISM: Typhlonectes natans

<400> SEQUENCE: 36

Met Asn Ser Thr Phe Ser Ser Glu Asp Arg Asp Pro Thr His Leu Ala
1               5                   10                  15

Ala Ile Asn His Ser Trp Gly Pro Val Glu Val Ala Ala Glu Thr Thr
            20                  25                  30

Arg Leu Asn Thr Thr His His Ser Glu Glu Val Phe Val Leu Pro Thr
        35                  40                  45

Phe Ser Thr Ala Ala Lys Val Arg Val Thr Ile Thr Phe Val Leu Phe
    50                  55                  60

Ile Ser Ser Ala Cys Phe Asn Ile Ile Ala Leu Trp Thr Ile Thr Gln
65                  70                  75                  80

Lys Tyr Lys Lys Arg Ser His Val Arg Ile Leu Ile Ser Asn Leu Ala
                85                  90                  95

Val Ala Asp Leu Leu Val Thr Phe Ile Val Met Pro Leu Asp Ala Ile
            100                 105                 110

Trp Asn Ile Thr Val Gln Trp Tyr Ala Gly Asp Leu Val Cys Arg Val
        115                 120                 125

Leu Met Phe Leu Lys Leu Val Ala Met Tyr Ala Ser Ala Phe Val Thr
    130                 135                 140

Val Val Ile Ser Leu Asp Arg Gln Ser Ala Ile Leu Asn Pro Leu Gly
145                 150                 155                 160

Ile Gly Asp Ala Lys Lys Lys Asn Lys Ile Met Leu Cys Val Ala Trp
                165                 170                 175
```

```
Val Leu Ser Val Leu Ala Val Pro Gln Leu Phe Val His Ala
            180                 185                 190

Val Ser Pro Ser Gln Ser Glu Tyr Phe Ile Gln Cys Ala Thr Val Gly
        195                 200                 205

Ser Phe Gln Gly His Trp Gln Glu Thr Leu Tyr Asn Met Phe Thr Phe
    210                 215                 220

Ser Cys Leu Phe Leu Pro Leu Leu Ile Met Val Leu Cys Tyr Ser
225                 230                 235                 240

Arg Ile Leu Ile Glu Ile Ser Arg Lys Met Lys Lys Ala Cys Val Ser
                245                 250                 255

Ser Lys Glu Val His Leu Arg Arg Ser Ser Asn Asn Ile Pro Lys Ala
            260                 265                 270

Arg Leu Arg Thr Leu Lys Met Ser Ile Val Ile Val Leu Thr Phe Ile
        275                 280                 285

Val Cys Trp Thr Pro Tyr Tyr Leu Leu Gly Ile Trp Tyr Trp Phe Ser
    290                 295                 300

Pro Glu Met Leu Thr Arg Glu Arg Val Pro Pro Ser Leu Ser His Ile
305                 310                 315                 320

Leu Phe Leu Phe Gly Leu Phe Asn Ala Cys Leu Asp Pro Leu Ile Tyr
                325                 330                 335

Gly Leu Phe Thr Ile His Phe Arg Arg Glu Ile Arg Arg Val Cys Arg
            340                 345                 350

Cys Arg Lys Gly Val Lys Glu Leu Asn Ile Ala Thr Gly Ser Phe Arg
        355                 360                 365

Val Ser Thr Ser Ala Val Pro Thr Gly Lys Ala Ser Gly Ala Gln Asn
    370                 375                 380

Gly Leu Glu Val Thr Gly Leu Asn Leu Gln Leu Gly Lys Cys Glu Gln
385                 390                 395                 400

Cys Arg Arg Lys Met Ala Glu Ser Phe Leu
                405                 410

<210> SEQ ID NO 37
<211> LENGTH: 407
<212> TYPE: PRT
<213> ORGANISM: Rana catesbeiana

<400> SEQUENCE: 37

Met Asn Ile Ser Lys Glu Val Ser Ile Lys Gly Cys Asn Asn Ala Gln
1               5                   10                  15

Trp Leu Ser Ser Cys Asp Leu Asp Val Asn Met Thr Ser Thr Asn
            20                  25                  30

Gly Thr His Thr His Phe Gln Leu Pro Thr Phe Ser Pro Ala Ala Lys
        35                  40                  45

Ala Arg Val Ile Ile Thr Phe Val Ile Phe Thr Leu Ser Ala Thr Cys
    50                  55                  60

Asn Leu Ala Ala Leu Trp Ser Ala Arg Thr Ser Arg Lys Lys Arg
65                  70                  75                  80

Ser His Val Arg Ile Leu Ile Leu Asn Leu Thr Thr Ala Asp Leu Leu
                85                  90                  95

Val Thr Phe Ile Val Met Pro Leu Asp Ala Ile Trp Asn Ile Thr Val
            100                 105                 110

Gln Trp His Ala Gly Asp Ile Ala Cys Arg Ile Leu Met Phe Leu Lys
        115                 120                 125

Leu Leu Ser Met Tyr Ser Cys Ala Phe Val Thr Val Val Ile Ser Val
    130                 135                 140
```

```
Asp Arg Gln Ser Ala Ile Leu Asn Pro Leu Ala Ile Asn Asp Ala Lys
145                 150                 155                 160

Lys Lys Asn Lys Ile Met Leu Ser Val Ala Trp Leu Met Ser Ala Val
            165                 170                 175

Leu Ser Leu Pro Gln Leu Phe Leu Phe His Thr Val Thr Ile Thr Glu
            180                 185                 190

Pro His Asn Phe Thr Gln Cys Thr Thr Arg Gly Ser Phe Gln Gln His
        195                 200                 205

Trp Gln Glu Thr Val Tyr Asn Met Val Ser Phe Val Cys Leu Phe Leu
    210                 215                 220

Leu Pro Leu Leu Ile Met Ile Cys Cys Tyr Ser Arg Ile Leu Leu Glu
225                 230                 235                 240

Ile Ser Lys Arg Met Ser Lys Gly Thr Leu Ser Ser Lys Glu Val Tyr
                245                 250                 255

Leu Arg Cys Ser Lys Asn Asn Ile Pro Lys Ala Arg Met Arg Thr Leu
            260                 265                 270

Lys Met Ser Val Val Ile Val Ser Ser Phe Ile Ile Cys Trp Thr Pro
        275                 280                 285

Tyr Phe Leu Leu Gly Leu Trp Tyr Trp Phe Tyr Pro Glu Ile Met Glu
    290                 295                 300

Glu Lys Val Ser Gln Ser Thr Thr His Ile Leu Phe Ile Phe Gly Leu
305                 310                 315                 320

Val Asn Ala Cys Leu Asp Pro Ile Thr Tyr Gly Leu Phe Thr Ile His
                325                 330                 335

Phe Arg Lys Ser Leu Gln Arg Tyr Cys Gly Gly Arg Arg Thr Ser Asp
            340                 345                 350

Ala Asp Thr Ser Ser Ser Val Thr Gly Ser Phe Arg Cys Ser Met Ser
        355                 360                 365

Ser Phe Arg Ala Lys Lys Met Ile Val Leu Asn Gln Glu Leu Gln Val
    370                 375                 380

Leu Gln Ser Cys Asn Gly Asn Phe Asn Asn Pro Glu Leu Arg Leu Asn
385                 390                 395                 400

Gly Leu Gly Thr Ser Cys Leu
                405

<210> SEQ ID NO 38
<211> LENGTH: 424
<212> TYPE: PRT
<213> ORGANISM: Rana catesbeiana

<400> SEQUENCE: 38

Met Asn Ala Ser Asp Gln Pro Met Gly Asp Gly Glu Ala Ala Pro Pro
1               5                   10                  15

Gly Leu Cys Ala Phe Lys Gly Phe Asn Phe Ser Cys Val His Ala Asn
            20                  25                  30

Gly Phe Glu Lys Pro His Gly Pro Asn Ile Thr Phe Leu Asn Glu Asp
        35                  40                  45

His Phe Val Leu Pro Thr Phe Ser Thr Ala Ala Lys Ile Arg Val Ala
    50                  55                  60

Ile Thr Cys Val Leu Phe Ile Ser Ser Ala Cys Phe Asn Met Ala Thr
65                  70                  75                  80

Leu Trp Thr Ile Thr Tyr Lys Tyr Arg Lys Lys Ser His Ile Arg Ile
                85                  90                  95

Leu Ile Ile Asn Leu Val Ala Ala Asp Leu Leu Ile Thr Phe Val Val
```

```
                100                 105                 110
Met Pro Leu Asp Ala Val Trp Asn Val Thr Ile Gln Trp Tyr Ala Gly
            115                 120                 125

Asp Val Ala Cys Arg Ile Leu Met Phe Leu Lys Leu Val Ala Met Tyr
        130                 135                 140

Ser Ser Ala Phe Val Thr Val Ile Ser Leu Asp Arg His Ala Ala
145                 150                 155                 160

Ile Leu Asn Pro Leu Gly Ile Gly Asp Ala Lys Lys Asn Lys Ala
                165                 170                 175

Met Leu Ser Val Ala Trp Thr Leu Ser Leu Leu Ala Thr Pro Gln
            180                 185                 190

Leu Phe Val Phe His Thr Val Ser Arg Ser Gln Pro Val His Phe Val
        195                 200                 205

Gln Cys Ala Thr Val Gly Ser Phe Lys Ala His Trp Leu Glu Thr Leu
    210                 215                 220

Tyr Asn Met Phe Thr Phe Cys Cys Leu Phe Leu Pro Leu Leu Ile
225                 230                 235                 240

Met Val Phe Cys Tyr Gly Arg Ile Leu Val Glu Ile Ser Arg Lys Met
                245                 250                 255

Lys Lys Ala Glu Val Ser Ser Arg Glu Val Asn Leu Arg Arg Ser Tyr
            260                 265                 270

Asn Asn Ile Pro Arg Ala Arg Met Arg Thr Phe Lys Met Ser Leu Val
        275                 280                 285

Ile Val Leu Thr Phe Ile Val Cys Trp Thr Pro Tyr Tyr Leu Leu Gly
    290                 295                 300

Ile Trp Tyr Trp Phe Ser Pro Glu Met Leu Thr Ser Arg Lys Val Pro
305                 310                 315                 320

Pro Ser Leu Ser His Ile Leu Phe Leu Phe Gly Leu Phe Asn Thr Cys
                325                 330                 335

Leu Asp Pro Ile Ile Tyr Gly Leu Phe Thr Ile His Phe Arg Arg Glu
            340                 345                 350

Ile Arg Arg Val Cys Arg Cys Ala Thr Gln Gly Lys Asp Ala Asp Ala
        355                 360                 365

Thr Ser Leu Gly Thr Gly Ser Phe Arg Ile Ser Thr Ala Ala Val Pro
370                 375                 380

Leu Lys Arg Ser Ala Gly Ala Ser Gly Gly Ser Cys Lys Phe Asp Leu
385                 390                 395                 400

Glu Val Thr Gly Val Gly Leu His Ser Gly Lys Cys Glu His Cys Lys
                405                 410                 415

Arg Gln Ile Val Glu Ser Phe Met
            420

<210> SEQ ID NO 39
<211> LENGTH: 419
<212> TYPE: PRT
<213> ORGANISM: Morone saxitilis

<400> SEQUENCE: 39

Met Asn Thr Thr Leu Cys Asp Ser Ala Val Ala Met Tyr His Leu Thr
1               5                   10                  15

Thr Asp His Gln Leu Asn Ala Ser Cys Asn Tyr Ser Ser Pro Thr Ser
            20                  25                  30

Asn Trp Thr Ser Gly Gly Gly Ser Leu Gln Leu Pro Thr Phe Thr Thr
        35                  40                  45
```

```
Ala Ala Lys Val Arg Val Ile Ile Thr Cys Ile Leu Cys Gly Ile Ser
     50                  55                  60

Ala Phe Cys Asn Leu Ala Val Leu Trp Ala Ala His Ser Asp Gly Lys
 65                  70                  75                  80

Arg Lys Ser His Val Arg Val Leu Ile Ile Asn Leu Thr Val Ala Asp
                 85                  90                  95

Leu Leu Val Thr Phe Ile Val Met Pro Val Asp Ala Val Trp Asn Ile
            100                 105                 110

Thr Val Gln Trp Leu Ala Gly Asp Leu Ala Cys Arg Leu Leu Met Phe
        115                 120                 125

Leu Lys Leu Gln Ala Met Tyr Ser Cys Ala Phe Val Thr Val Val Ile
130                 135                 140

Ser Leu Asp Arg Gln Ser Ala Ile Leu Asn Pro Leu Ala Ile Asn Lys
145                 150                 155                 160

Ala Arg Lys Arg Asn Arg Val Asn Leu Thr Val Ala Trp Gly Met Ser
                165                 170                 175

Val Val Leu Ser Val Pro Gln Leu Phe Leu Phe His Asn Val Thr Ile
            180                 185                 190

Ile Tyr Pro Glu Asp Phe Thr Gln Cys Thr Thr Arg Gly Ser Phe Val
        195                 200                 205

Thr His Trp His Glu Thr Ala Tyr Asn Met Phe Thr Phe Ser Cys Leu
210                 215                 220

Phe Leu Leu Pro Leu Ile Ile Met Ile Thr Cys Tyr Thr Arg Ile Phe
225                 230                 235                 240

Cys Glu Ile Ser Lys Arg Leu Lys Lys Asp Asn Leu Pro Ser Asn Glu
                245                 250                 255

Val His Leu Arg Arg Ser Lys Asn Asn Ile Pro Arg Ala Arg Met Arg
            260                 265                 270

Thr Leu Lys Met Ser Ile Val Ile Val Ser Ser Phe Ile Val Cys Trp
        275                 280                 285

Thr Pro Tyr Tyr Leu Leu Gly Leu Trp Tyr Trp Phe Phe Pro Asp Asp
290                 295                 300

Leu Glu Gly Lys Val Ser His Ser Leu Thr His Ile Leu Phe Ile Phe
305                 310                 315                 320

Gly Leu Val Asn Ala Cys Leu Asp Pro Val Ile Tyr Gly Leu Phe Thr
                325                 330                 335

Ile His Phe Arg Lys Gly Leu Arg Arg Tyr Tyr Cys Asn Ala Thr Lys
            340                 345                 350

Ala Ser Asp Leu Asp Asn Asn Thr Val Ile Thr Gly Ser Phe Ile Cys
        355                 360                 365

Ala Ala Asn Ser Leu Pro Leu Lys Arg Glu Val Ser Pro Ala Ser Gln
370                 375                 380

Glu Arg Phe Val Leu Tyr Ser Asp Asn His Ser Arg Ala Glu Leu Thr
385                 390                 395                 400

Ser Pro Arg Ser Ser Phe Leu Arg Asp Pro Asn Gln Ser Ser Ser Glu
                405                 410                 415

Ser Asn Leu

<210> SEQ ID NO 40
<211> LENGTH: 375
<212> TYPE: PRT
<213> ORGANISM: Gallus gallus

<400> SEQUENCE: 40
```

```
Met Cys Val Pro Ala Ala Leu Ile Glu Ala Glu Pro His His Pro
  1               5                  10                  15

Thr Thr Glu Gly Asp Thr Asn Thr Ser Ala Thr His Cys Leu Glu His
                    20                  25                  30

Trp Val Glu Pro Arg Phe Thr Lys Ala Ala Lys Val Arg Val Ala Ile
                35                  40                  45

Thr Ala Val Phe Phe Leu Leu Ala Ala Cys Ser Asn Thr Ala Val Leu
         50                  55                  60

Gly Ser Leu Leu Arg Lys Arg Arg Lys Cys His Val Arg Pro Leu Ile
 65                  70                  75                  80

Leu Ser Leu Ala Leu Ala Asp Leu Leu Val Thr Val Ala Val Met Pro
                 85                  90                  95

Leu Asp Ala Ala Trp Asn Val Thr Val Gln Trp Tyr Gly Gly Asp Leu
                100                 105                 110

Ser Cys Lys Leu Leu Asn Phe Leu Lys Leu Phe Ala Met Tyr Ala Ala
                115                 120                 125

Ala Leu Val Leu Val Val Ile Ser Leu Asp Arg His Ala Ala Val Leu
130                 135                 140

Gln Pro Phe Ala Arg Ala Arg Arg Asn Gly Leu Leu Leu Arg Ala
145                 150                 155                 160

Ala Trp Leu Gly Ser Val Leu Leu Ala Ser Pro Gln Leu Phe Leu Phe
                165                 170                 175

His Val His Thr Val Pro Gly Gly Asn Phe Thr Gln Cys Val Thr His
                180                 185                 190

Gly Ser Phe Arg Ala His Trp Glu Glu Thr Val Tyr Asn Met Phe Thr
                195                 200                 205

Phe Thr Thr Leu Tyr Ile Thr Pro Leu Ser Ile Met Ile Val Cys Tyr
210                 215                 220

Val Arg Ile Ile Trp Glu Ile Ser Lys Gln Leu Lys Ile Asn Lys Ser
225                 230                 235                 240

Leu Val Arg Ser Gln Asn Asp His Ile Ser Lys Ala Arg Met Lys Thr
                245                 250                 255

Leu Lys Met Thr Ile Val Ile Val Ala Ser Phe Ile Ile Cys Trp Thr
                260                 265                 270

Pro Tyr Tyr Leu Leu Gly Leu Trp Tyr Trp Phe His Pro Ala Met Ile
                275                 280                 285

Gln Arg Met Pro Glu Tyr Ile Asn His Ser Phe Phe Leu Phe Gly Leu
290                 295                 300

Leu His Thr Cys Thr Asp Pro Ile Ile Tyr Gly Leu Tyr Thr Pro Ser
305                 310                 315                 320

Phe Arg Glu Asp Val Gln Leu Cys Leu Arg Gly Ile Glu Ala Ala Ile
                325                 330                 335

Ser Gln His Val Arg His Lys Pro Ile Ser Val Ser Glu Lys Thr Thr
                340                 345                 350

Lys Asp Gly Asp Val Asn Gly Gln Val Thr Ser Gly Ser Asn Gly
                355                 360                 365

Thr Thr Val Asn Thr Val Cys
    370                 375

<210> SEQ ID NO 41
<211> LENGTH: 328
<212> TYPE: PRT
<213> ORGANISM: Homo sapiens

<400> SEQUENCE: 41
```

```
Met Ala Asn Ser Ala Ser Pro Glu Gln Asn Gln Asn His Cys Ser Ala
 1               5                  10                  15

Ile Asn Asn Ser Ile Pro Leu Met Gln Gly Asn Leu Pro Thr Leu Thr
            20                  25                  30

Leu Ser Gly Lys Ile Arg Val Thr Val Thr Phe Phe Leu Phe Leu Leu
        35                  40                  45

Ser Ala Thr Phe Asn Ala Ser Phe Leu Leu Lys Leu Gln Lys Trp Thr
    50                  55                  60

Gln Lys Lys Glu Lys Gly Lys Lys Leu Ser Arg Met Lys Leu Leu Leu
65                  70                  75                  80

Lys His Leu Thr Leu Ala Asn Leu Leu Glu Thr Leu Ile Val Met Pro
                85                  90                  95

Leu Asp Gly Met Trp Asn Ile Thr Val Gln Trp Tyr Ala Gly Glu Leu
               100                 105                 110

Leu Cys Lys Val Leu Ser Tyr Leu Lys Leu Phe Ser Met Tyr Ala Pro
           115                 120                 125

Ala Phe Met Met Val Val Ile Ser Leu Asp Arg Ser Leu Ala Ile Thr
       130                 135                 140

Arg Pro Leu Ala Leu Lys Ser Asn Ser Lys Val Gly Gln Ser Met Val
145                 150                 155                 160

Gly Leu Ala Trp Ile Leu Ser Ser Val Phe Ala Gly Pro Gln Leu Tyr
                165                 170                 175

Ile Phe Arg Met Ile His Leu Ala Asp Ser Ser Gly Gln Thr Lys Val
               180                 185                 190

Phe Ser Gln Cys Val Thr His Cys Ser Phe Ser Gln Trp Trp His Gln
           195                 200                 205

Ala Phe Tyr Asn Phe Phe Thr Phe Ser Cys Leu Phe Ile Ile Pro Leu
       210                 215                 220

Phe Ile Met Leu Ile Cys Asn Ala Lys Ile Ile Phe Thr Leu Thr Arg
225                 230                 235                 240

Val Leu His Gln Asp Pro His Glu Leu Gln Leu Asn Gln Ser Lys Asn
                245                 250                 255

Asn Ile Pro Arg Ala Arg Leu Lys Thr Leu Lys Met Thr Val Ala Phe
               260                 265                 270

Ala Thr Ser Phe Thr Val Cys Trp Thr Pro Tyr Tyr Val Leu Gly Ile
           275                 280                 285

Trp Tyr Trp Phe Asp Pro Glu Met Leu Asn Arg Leu Ser Asp Pro Val
       290                 295                 300

Asn His Phe Phe Phe Leu Phe Ala Phe Leu Asn Pro Cys Phe Asp Pro
305                 310                 315                 320

Leu Ile Tyr Gly Tyr Phe Ser Leu
                325

<210> SEQ ID NO 42
<211> LENGTH: 45
<212> TYPE: DNA
<213> ORGANISM: Artificial sequence
<220> FEATURE:
<223> OTHER INFORMATION: Description of Artificial Sequence: Synthetic
      nucleotide construct

<400> SEQUENCE: 42
aactggaaga attcgcggcc gcaggaattt ttttttttt ttttt            45
```

CLONING AND EXPRESSION OF GONADOTROPIN-RELEASING HORMONE (GNRH) RECEPTORS

CROSS-REFERENCE TO RELATED APPLICATIONS

The present application claims the benefit of Provisional Application Ser. No. 60/561,006 filed Apr. 9, 2004, which is incorporated herein by reference.

GOVERNMENT SPONSORSHIP

This Invention is funded in part by NSF grant Nos. IBN-0090852 and IBN-9722765.

COPYRIGHT

A portion of the disclosure of this patent document contains material that is subject to copyright protection. The copyright owner has no objection to the facsimile reproduction by anyone of the patent document or the patent disclosure as it appears in the United States Patent and Trademark Office patent file or records, but otherwise reserves all copyright rights whatsoever.

SEQUENCE LISTING

The Sequence Listing submitted on compact disc containing the file named "Sequence Listing Full Application" which has a size of 103 KB created on Jul. 11, 2005 are herein incorporated by reference.

FIELD OF THE INVENTION

The invention relates to hormone receptors, more particularly, to a gonadotropin-releasing hormone (GnRH) protein, production and use thereof.

BACKGROUND OF THE INVENTION

In vertebrates, the hypothalamus and pituitary have well-defined roles in the control of reproduction. Gonadotropin-releasing hormone ("GnRH") is the central regulatory neurohormone controlling reproduction in all vertebrates. GnRH is a ten amino-acid peptide, synthesized in the hypothalamus, and released into the hypophysial portal blood system, directly into the pituitary gland as in the case of teleost fish, or by diffusion as in the case of Agnathans. Upon response to external cues (such as environmental cues like water temperature) and internal cues, GnRH is released and acts at the pituitary gland to stimulate the synthesis and release of the gonadotropins, which then travel by systemic circulation to the gonads, thereby regulating steroidogenesis and gametogenesis.

GnRH action at the pituitary is mediated by specific, high-affinity receptors; these GnRH receptors are 7-transmembrane-domain (7-TM) G protein-coupled receptors (GPCRs). 7-TM GPCRs are one of the most abundant families of proteins in the human genome, and they mediate a large portion of the cellular signals necessary for life. The GnRH receptors are the only subgroup within this protein family in which certain members lack an important structural feature: the intracellular, C-terminal tail. Many studies have demonstrated the importance of this intracellular domain for proper activity and regulation of receptors, and within the GnRH family this structural variance is thought to be one of the central features contributing to GnRH signal integration and gonadotropin control.

Lamprey

The GnRH system has been studied in several species in examining the evolution of reproductive biology; one of these species is the sea lamprey. Lampreys and hagfish, of the Class Agnatha, are of particular importance in understanding endocrinological relationships since they are the modern descendants of the most primitive vertebrates. They represent the oldest lineages of extant vertebrates—which evolved over 550 million years ago. Therefore, the study of lampreys and the characterization of brain and pituitary hormones in lampreys are particularly important for understanding the molecular evolution and functional diversity of reproductive hormones, and can potentially yield valuable insight into human reproductive processes.

Until about 20 years ago, there was question as to whether there was brain control of reproduction in lampreys. Extensive molecular, biochemical, and physiological studies have demonstrated that reproductive development and function are regulated by two hypothalamic GnRH isoforms, lamprey GnRH-I and lamprey GnRH-III. Thus, in addition to commercial and medical values discussed below, the study of lamprey reproduction can shed light on the overall evolution of vertebrate reproduction.

GnRH

GnRH is the central controlling hormone of the hypothalamo-hypophysial-gonadal axis across all vertebrates. Its action modulates the function of the entire reproductive system through its regulation of this axis. The GnRH decapeptide is produced in cell bodies located in the hypothalamus of the brain. Axons from these cell bodies extend caudally, where they impinge on the median eminence (a neuro-hemal organ, which serves as a blood portal system between the hypothalamus and the pituitary) in mammals, the pituitary in teleost fish, or a thin layer of epithelial tissue just above the pituitary in Agnathans. GnRH is released from the axon terminals of these hypothalamic neurons and travels (by diffusion in Agnathans) to the pituitary where it binds specific receptors on the exterior of pituitary gonadotrope cells. Upon GnRH binding, the receptor activates a signal transduction cascade, which causes the release of gonadotropins, luteinizing hormone (LH) and follicle stimulating hormone (FSH) in later evolved vertebrates, or their equivalents in earlier evolved vertebrates. These gonadotropins are released into the bloodstream and travel via the circulatory system to the gonads, where they regulate gonadal development and gonadal function. This mechanism of GnRH action has been shown to exist in representative members of all vertebrate classes.

With the recent identification of multiple GnRH receptors in the pituitary and evidence of multiple hypothalamic GnRH isoforms in primates, understanding the integration of this system will be critical to effective modulation for medical treatments and for reduction of side-effects. One of the most important aspects of this investigation will be to understand the implications of the vast structural differences between the tailed and tail-less GnRH receptors and to understand the different interactions of the multiple receptors with the different GnRH isoforms. The lamprey GnRH receptor will prove invaluable to such study.

Thus, it would be desirable to have the DNA and amino acid sequences of a lamprey GnRH receptor, and to make and use such receptor for animal and human research and therapeutic applications including production of GnRH analogs, cancer treatment, and reproductive treatment and therapy for animals and humans. The lamprey GnRH receptor and its DNA and amino acid sequences will be invaluable in the design of such compounds.

SUMMARY OF THE INVENTION

In accordance with one aspect of the present invention, an isolated and purified GnRH protein receptor protein including an amino acid sequence represented by SEQ ID NO: 2 and its substantial equivalents thereto, or a salt thereof.

In accordance with one aspect of the present invention, an isolated and purified DNA which comprises a nucleotide sequence coding for the GnRH protein receptor protein including a nucleotide sequence represented by SEQ ID NO: 1. In accordance with another aspect of the present invention, a vector comprising the DNA of the GnRH protein receptor protein having the nucleotide sequence represented by SEQ ID NO: 1. In accordance with another aspect of the present invention, a transformant carrying the vector comprising the DNA of the GnRH protein receptor protein.

In accordance with another aspect of the present invention, a process for producing a GnRH protein receptor protein or a salt thereof including culturing the transformant carrying the vector comprising the DNA of the GnRH protein receptor protein under sufficient conditions and for appropriate time to express the GnRH protein receptor protein.

Some embodiments of this aspect of the invention further include allowing the GnRH protein receptor protein or salt thereof to accumulate, and collecting the GnRH protein receptor protein or a salt thereof.

In accordance with another aspect of the present invention a method of screening for a ligand to the GnRH protein receptor protein including contacting the GnRH protein receptor protein or a salt thereof with a sample to be tested.

In accordance with another aspect of the present invention, a screening method for a compound capable of inhibiting binding of the GnRH protein receptor protein with a ligand, including conducting a comparison between: at least one case where the ligand is contacted with the GnRH protein receptor protein or a salt thereof, and at least one case where the ligand together with a sample to be tested is contacted with the GnRH protein receptor protein or a salt thereof and determining difference in binding activity.

In accordance with another aspect of the present invention, a kit for screening a compound capable of inhibiting binding of the GnRH protein receptor protein with a ligand including the GnRH protein receptor protein or a salt.

Some embodiments of this aspect of the invention further include one or more of the following. An antibody which specifically binds to the GnRH protein receptor protein or a salt thereof. A reagent for probing a GnRH protein receptor protein including DNA.

These aspects of the invention are not meant to be exclusive and other features, aspects, and advantages of the present invention will be readily apparent to those of ordinary skill in the art when read in conjunction with the following description, appended claims and accompanying drawings.

BRIEF DESCRIPTION OF THE DRAWINGS

TABLE 1 shows the lamprey GnRH receptor (GSP's) Gene Specific Primers (SEQ. ID. NOS. 7-34) used in the invention. GSP's 2, 4, 6, 8, 10, 23 and 24 are 3'→5' (antisense) primers, and all others are 5'→3' (sense) primers.

FIG. 1 is the DNA sequence map of the lamprey GnRH receptor of the invention (SEQ ID NO: 1). The lamprey GnRH receptor transcript is shown with the amino acid coding sequence of the predicted protein (SEQ ID NO: 2). (N-term=amino-terminal tail, IC=intracellular loop, TM=transmembrane domain, EC=extracellular loop, C-term=carboxyl-terminal tail).

DETAILED DESCRIPTION OF THE INVENTION

Figure 2:
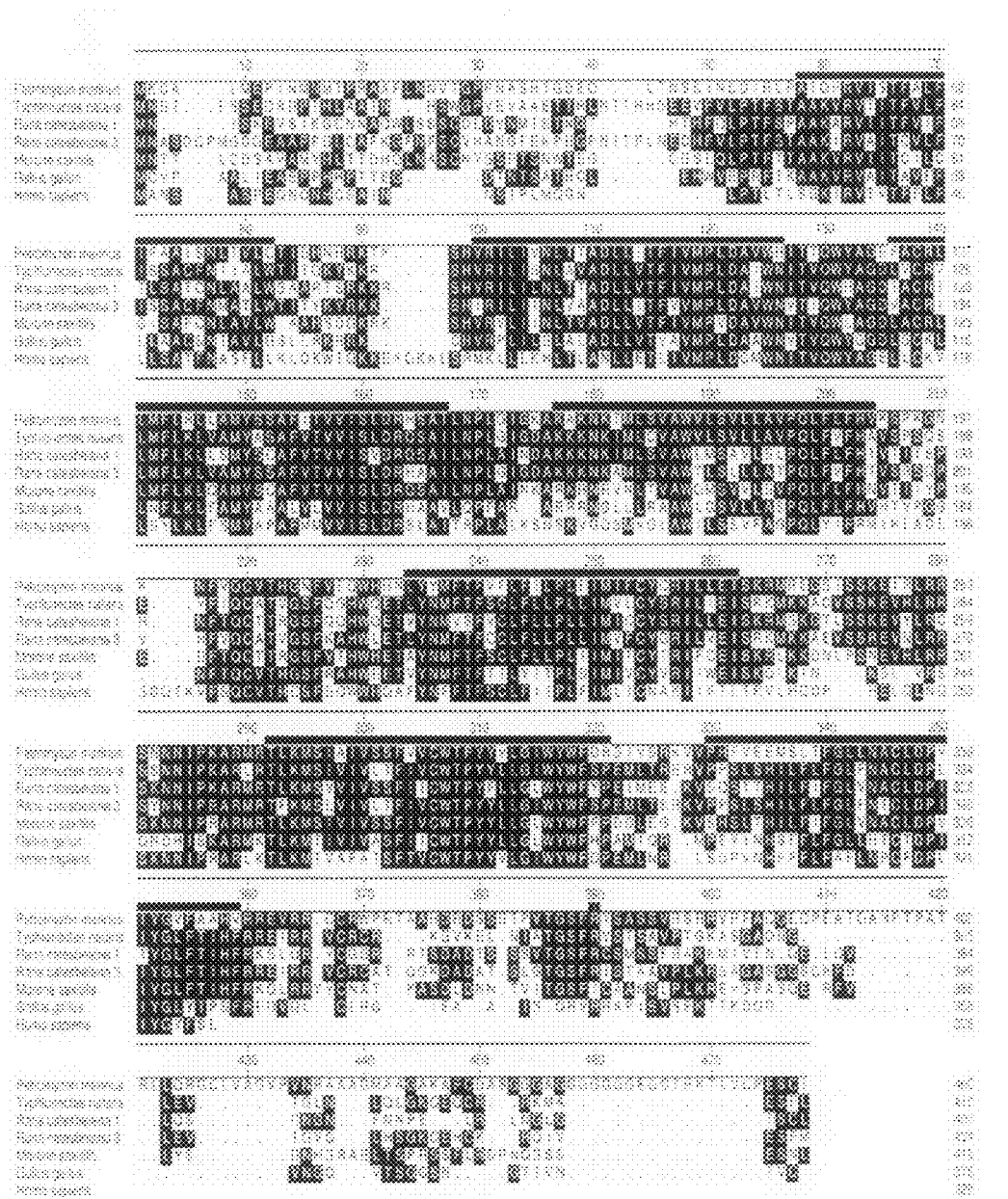
FIG. 2 shows the amino acid alignment of lamprey GnRH receptor with representative GnRH-R's (GnRH Receptors). Shaded amino acids are shared with the consensus formed from this alignment (consensus not shown). Black bars above the sequence indicate transmembrane domains (SEQ ID NOS 2, and 36-41 respectively, from top to bottom).

The invention is the isolation, purification and sequencing of a lamprey gonadotropin-releasing hormone receptor. The invention includes the cDNA sequence for a novel gonadotropin-releasing hormone receptor in lamprey. Also included in the invention is the deduced amino acid sequence of the novel lamprey gonadotropin-releasing hormone receptor, as well as biologically equivalent analogs of the receptor. Also included are mutant or polymorphic forms of the receptor and recombinant nucleic acids encoding the same. The invention also includes applications, uses, and methods of expressing, making and using the novel lamprey gonadotropin-releasing hormone receptor, its cDNA, deduced amino acid sequence and biologically equivalent analogs of the receptor. Also included are assays employing the receptor gene products, including genetically engineered host cells which express the receptor, antibodies against the receptor and polypeptides thereof, and modulators, agonistic and/or antagonistic compounds identified though the use of assays utilizing the receptor gene products including, but not limited to one or more compounds or molecules that act through direct or indirect contact with a ligand which either interacts with the receptor or with the transcription or translation of GnRH, thereby modulating GnRH expression. The invention also includes uses of the receptor, recombinant nucleic acids and recombinant host cells for drug screening and development, diagnosis, and therapeutic applications in animals and humans including research such as evolutionary studies, investigating the C-terminal tail, and reproductive research in animals and humans including identifying homologous receptors in other vertebrates.

Applicants have isolated and sequenced a novel cDNA, the cDNA encoding lamprey a gonadotropin-releasing hormone (GnRH) receptor. The present invention provides previously unknown isolated cDNA which encodes a lamprey GnRH receptor, and the amino acid sequence of the receptor.

Each document mentioned in this specification is hereby incorporated herein by reference in its entirety.

The GnRH system has been studied in several species in examining the evolution of reproductive biology; one of these species is the sea lamprey. Lampreys and hagfish, of the Class Agnatha, are of particular importance in understanding endocrinological relationships since they are the modern descendants of the most primitive vertebrates. They represent the oldest lineages of extant vertebrates—which evolved over 550 million years ago. Therefore, the study of lampreys and the characterization of brain and pituitary hormones in lampreys are particularly important for understanding the molecular evolution and functional diversity of reproductive hormones, and can potentially yield valuable insight into human reproductive processes.

Until about 20 years ago, there was question as to whether there was brain control of reproduction in lampreys. Extensive molecular, biochemical, and physiological studies have demonstrated that reproductive development and function are regulated by two hypothalamic GnRH isoforms, lamprey GnRH-I and lamprey GnRH-III. Thus, in addition to commercial and medical values discussed below, the study of lamprey reproduction can shed light on the overall evolution of vertebrate reproduction.

GnRH

GnRH is the central controlling hormone of the hypothalamo-hypophysial-gonadal axis across all vertebrates. Its action modulates the function of the entire reproductive system through its regulation of this axis. The GnRH decapeptide is produced in cell bodies located in the hypothalamus of the brain. Axons from these cell bodies extend caudally, where they impinge on the median eminence (a neuro-hemal organ, which serves as a blood portal system between the hypothalamus and the pituitary) in mammals, the pituitary in teleost fish, or a thin layer of epithelial tissue just above the pituitary in Agnathans. GnRH is released from the axon terminals of these hypothalamic neurons and travels (by diffusion in Agnathans) to the pituitary where it binds specific receptors on the exterior of pituitary gonadotrope cells. Upon GnRH binding, the receptor activates a signal transduction cascade, which causes the release of gonadotropins, luteinizing hormone (LH) and follicle stimulating hormone (FSH) in later evolved vertebrates, or their equivalents in earlier evolved vertebrates. These gonadotropins are released into the bloodstream and travel via the circulatory system to the gonads, where they regulate gonadal development and gonadal function. This mechanism of GnRH action has been shown to exist in representative members of all vertebrate classes.

There is growing evidence to indicate that almost all vertebrates synthesize at least two isoforms of GnRH. Typically, the neuroendocrine form is present in the hypothalamus and acts at the level of the pituitary. The second form is generally extra-hypothalamic and acts as a neurotransmitter in some unknown functions. Lampreys, representatives of the oldest lineage of vertebrates, are the first vertebrates in which two hypothalamic GnRHs, lamprey GnRH-I and lamprey GnRH-III, were found to regulate the pituitary. Lampreys are also the first vertebrates in which the presence of two high-affinity GnRH binding sites was clearly demonstrated in the pituitary[7]. These findings strongly suggest that at least two functional GnRH receptors exist within the lamprey pituitary.

In addition to conservation of the GnRH mechanism, the decapeptide has been highly conserved. Since the first landmark identification and sequencing of the mammalian form of GnRH from the pig and sheep by Schally and Guillemin, there have been twenty-four (24) different isoforms identified, fourteen (14) in vertebrates and ten (10) in invertebrates.

The evolutionary conservation of the GnRH family of peptides is evident; none differs by more than 50%. The N-terminal, $Ser^4$, and C-terminal regions have remained unchanged, while amino acids 5-8 are more highly variable with the greatest variability in the eighth position. Computer modeling studies of the mammal GnRH peptide have shown that the most likely conformation is a bent structure in which the GnRH molecule assumes an 180° β-turn through amino acids 5-8. Such a structure would suggest that the amino acids forming this β-turn need only form the proper conformation; side chain interactions may be less important. These conformational studies along with numerous GnRH analog studies indicate that the most highly conserved N- and C-terminal amino acids are the portions of the molecule that interact directly with the GnRH receptor. The data from these studies have established a picture of the GnRH importance and constraints on each of the amino acid positions within the decapeptide.

Interestingly, computer modeling of the most probable solution conformations of GnRH peptides suggests that GnRH isoforms with lysine in the eighth position, such as the lamprey GnRH isoforms, are likely to assume a much different form than that described by Sealfon in 1997. This difference in conformation indicates that a different receptor-activating interaction likely occurs with these GnRH isoforms. A study by Sower, et al. demonstrated that lamprey GnRH-I, when cyclized to form the traditionally expected β-turn conformation, showed reduced capacity to elevate blood plasma estradiol levels as compared to native lamprey GnRH-I. This is a very significant finding, as it suggests that the lamprey GnRH isoforms activate their receptors through a different interaction than mammal GnRH. This is of particular interest because there is evidence of a lamprey GnRH-III-like isoform present and functioning in other vertebrates, particularly mammals.

Multiple studies have demonstrated activity of lamprey GnRH-III in other fish as well as in certain mammalian species and cell lines. In rats, Yu et al. demonstrated that lamprey GnRH-III has a potent, dose-related FSH-, but not LH-, releasing action on incubated hemipituitaries of male rats. Lamprey GnRH-I on the other hand, had little activity to release either FSH or LH. From these and later studies, McCann and colleagues have postulated that a molecule close to lamprey GnRH-III may be the long sought-after FSH releasing factor in mammals. Most recently, utilized a newly developed antiserum (provided by Dr. Stacia Sower), specific for lamprey gonadotropin-releasing hormone III (1-GnRH-III), to determine that, unlike other isoforms of GnRH found in the mammalian brain, lamprey GnRH-III neurons not only are observed in regions that control follicle-stimulating hormone release but also are colocalized with mammalian GnRH neurons in areas primarily controlling LH release. These findings suggest an interrelationship between these two peptides in the control of gonadotropin secretion. This suggested interrelationship and the indicated unique mechanism of receptor activation by the lamprey GnRH isoforms give the lamprey GnRH receptor particular value in the study of GnRH mechanisms in lampreys as well as other vertebrates.

GnRH Receptor

In light of the crucial role GnRH plays in human physiology and disease, its receptor has been a subject of intense research for many years. Many studies on the binding characteristics of the GnRH receptor were performed throughout the 1970's and 1980's. In 1992, Tsutsumi, et al. reported the first successful cloning of a GnRH receptor from the mouse using a homology-based PCR amplification scheme. Later that year, a human GnRH receptor cDNA was reported as well. Both of these sequences were soon confirmed using slightly different methods. Analysis of the sequence of the first known GnRH receptors identified them as members to the G protein-coupled superfamily of receptors (GPCR). GnRH action is mediated through a Class A rhodopsin-like 7-transmembrane G protein-coupled receptor (GPCR). The members of this superfamily share a common general structure composed of seven hydrophobic α-helical transmembrane domains connected by hydrophilic protein loops, an extracellular N-terminal tail, and an intracellular C-terminal tail. Known GnRH receptors share a number of unique features that distinguish them from other Class A GPCRs, including variations of the conserved transmembrane domain motifs, and most distinctly, the evolutionary loss of the C-terminal tail in certain mammalian GnRH receptors. Since the first successful cloning of a GnRH receptor transcript from the mouse, a total of 39 GnRH receptor cDNAs have been identified in 27 organisms: 14 in mammals and 25 in earlier evolved vertebrates. The tailed receptors known to date contain intracellular tails of sizes varying from about 40-80 amino acids in length.

The GnRH receptor family is unique among G protein-coupled receptors because a number of its members lack an intracellular C-terminal tail. All of these tail-less receptors have been identified from mammalian species, and since some of these were the first GnRH receptors identified, it was originally thought that all GnRH receptors lacked a C-terminal tail. In 1997, the first tailed GnRH receptor was identified in the African catfish. Since then, 5 more mammalian tail-less receptors, 24 non-mammalian tailed receptors, and most recently, 3 mammalian tailed receptors have been described. The extensive cloning of GnRH receptors from various species has enabled researchers to explore the structure-function aspects of the receptors and how their differences and similarities provide insight into the complex integration and function of the GnRH system. Many studies have investigated the importance of the C-terminal tail in receptor signaling, internalization, desensitization, and expression. Recent studies have demonstrated that the presence or absence of the C-terminal tail in GnRH receptors can completely change the desensitization pathways of these receptors, as well as modify their signaling and binding properties.

The C-terminal tail has been shown to affect not only effective GnRH binding and activation of signal 3 transduction, but desensitization and internalization pathways as well. Three GnRH receptor subtypes: IA, IB, and II; have been suggested based on phylogenetic and sequence analysis of extracellular loop 3. Because the main physiological role of the GnRH receptor is to mediate GnRH control of gonadotropin release from the pituitary, GnRH receptor expression within the pituitary has been investigated extensively. Early studies, using autoradiography to map GnRH binding sites within the pituitary, focused on the rat as the primary model. By combining GnRH autoradiography with lactotroph-labeling, these studies showed that the GnRH binding sites are localized within the anterior pituitary on gonadotropin-producing cells.

Further studies used radioligand binding assays with pituitary membrane preparations to examine GnRH binding sites in the pituitaries of mammals and fish, thereby characterizing the binding affinities and competitive binding of various analogs. A single class of high-affinity binding sites was identified in the pituitary of the seabream, mouse, rat, hamster, ewe, and rhesus monkey. Two classes of pituitary binding sites, one high-affinity/low-capacity and one low-affinity/high-capacity, were described in the cow, rabbit, and goldfish. Once cDNAs for GnRH receptors were identified, in situ hybridization was used by some groups to map the expression of GnRH receptors within the pituitary. Studies in the mouse, marmoset, and stump-tailed macaque have shown widely distributed expression of the type I GnRH receptor in the anterior pituitary. In situ hybridization in the rainbow trout has similarly demonstrated pituitary GnRH receptor expression concentrated in the proximal pars distalis, while both goldfish GnRH receptor transcripts were also visualized primarily in the proximal pars distalis.

Recently, multiple GnRH receptors have been characterized in several species, suggesting that most organisms likely contain two or more functional GnRH receptors in the pituitary and brain. Investigations in these organisms have demonstrated differential tissue distribution of GnRH receptor subtypes, as well as changes in receptor transcript expression based on reproductive stage. While the representation of GnRH receptors across the vertebrate lineage extends from mammals to Osteichthyes, there have not yet been any GnRH receptors isolated and cloned in earlier evolved vertebrates from Chondrichthyes or Agnatha.

Studies in recent years have demonstrated that unique variations in GnRH receptor structure as well as the presence of multiple receptor forms in the same cell populations in individual species are important aspects of the GnRH system that must be investigated. Since the identification of two distinct GnRH receptor isoforms in the goldfish in 1999, multiple GnRH receptors have been identified in two species of frog, in the African catfish, as well as in primates. While all of the GnRH receptors identified in frogs, goldfish, and catfish are tailed receptors, in primates both a tail-less and a tailed receptor have been identified. These multiple-receptor systems not only suggest a complex integration for proper GnRH signaling, but offer more importance to the presence or absence of the C-terminal tail in this integration. Applicants have previously characterized two high-affinity GnRH binding sites in the lamprey pituitary, suggesting the presence of at least two functional GnRH receptors in the lamprey pituitary.

Lampreys, along with hagfish, represent the only surviving members of the class Agnathans, the oldest extant vertebrates. This ancient lineage diverged from the main vertebrate line over 550 million years ago. Lampreys are important to the understanding of the reproductive success of the first vertebrates and are likely to have retained the key characteristics of the ancestral GnRH and GnRH receptor from which modern GnRH isoforms and GnRH receptors arose. Two GnRH isoforms have been identified in the brain of the lamprey. These two GnRH isoforms are the only vertebrate forms that vary in the sixth position, and lamprey GnRH-III is the only isoform known to vary in the third position, containing a Tyr instead of the characteristic Trp. Applicants' previous work has included physiological, anatomical, biochemical, and molecular studies on lamprey GnRH-I and lamprey GnRH-III, which have provided overwhelming evidence that these two GnRH isoforms control lamprey reproduction via regulation of the hypothalamo-pituitary-gonadal axis.

As part of these studies, two distinct GnRH binding sites have been characterized in the pituitary of the adult lamprey by quantitative in vitro autoradiography. Scatchard analysis identified high affinity binding sites with Kds of $1.5 \times 10^{-12}$ and $5 \times 10^{-9}$. The binding sites were concentrated in the proximal pars distalis, and small amounts of specific binding were visualized in the rostral pars distalis. Two classes of high affinity GnRH binding sites were also characterized in the lamprey pituitary during the parasitic phase of the lamprey life cycle, as well as during the course of gonadal maturation. These two classes of high affinity pituitary binding sites increased in concentration as the lampreys sexually matured.

GnRH Applications

GnRH has been the subject of intense research for many years because of its dual significance for understanding reproductive biology and for developing medical therapies. Aside from its importance in research for understanding reproductive biology, GnRH has many medical and other practical applications including reproductive enhancement and/or contraception in animals and fishes. In fact, GnRH and its analogs are already being used in commercial fish farming to stimulate and regulate sexual maturation and reproduction. The various GnRH receptors that have been identified across vertebrates have added vast amounts of information for improved design of new GnRH analogs for both commercial and medical uses.

There are also many potential therapeutic human reproductive applications for GnRH. Since 1971 when the primary structure of mammalian GnRH was determined, over 7,000 analogs to GnRH have been made and tested in hundreds of studies in mammals. So far, the most active synthetic agonists are found to be those with D-amino acid substitution in position 6 of the GnRH decapeptide. The most effective GnRH antagonists to date are those that have substitutions in position 6 as well as substitution of amino acids in positions 1, 2, and 3.

As a result of these studies several mammalian GnRH analogs have been shown to be highly successful and are currently being used for sterilization, conception and other therapeutic and clinical applications. There is considerable interest in the function of each residue in the GnRH so that analogs can be designed with maximum efficiency as agonists or antagonists to the GnRH receptor, for use as drugs. Furthermore, the responses to GnRH and analogs are different in males compared to females, suggesting that different neuroendocrine mechanisms may be involved.

To date, many GnRFI analogs have proven useful, but produce undesirable side effects, such as affecting more than just the target. For example, LUPRON DEPOT® which is a GnRH analog and is now one of the leading chemical treatments for advanced prostate cancer and endometriosis in humans, has undesirable side effects. Continuous treatment of LUPRON DEPOT® results in decreased levels of luteinizing hormone (LH) and follicle stimulating hormone (FSH). In males, testosterone is reduced to castrate levels. In pre-menopausal females, estrogens are reduced to post-menopausal levels;

With the recent identification of multiple GnRH receptors in the pituitary and evidence of multiple hypothalamic GnRH isoforms in primates, understanding the integration of this system will be critical to effective modulation for medical treatments and for reduction of side-effects. One of the most important aspects of this investigation will be to understand the implications of the vast structural differences between the tailed and tail-less GnRH receptors and to understand the different interactions of the multiple receptors with the different GnRH isoforms. The lamprey GnRH receptor disclosed herein will prove invaluable to such study.

With respect to the present invention, the following terms are used herein.

A "compound" or "molecule" is any organic or inorganic assembly of atoms, that can include macromolecules such as peptides, polypeptides, whole proteins, and polynucleotides.

An "agonist" is a compound or molecule that interacts and activates a polypeptide of a receptor.

An "antagonist" is a compound or molecule that interacts with and inhibits or prevents a polypeptide of a receptor from becoming activated.

A "modulator" is a compound or molecule that interacts with an aspect of cellular biochemistry to effect an increase or decrease in the amount of a polypeptide of a receptor present at the surface of a cell, or in the surrounding serum or media. The change in amount of the receptor polypeptide can be mediated by the effect of a modulator on the expression of the receptor, e.g. the transcription, translation, post-translational processing, translocation or folding of the receptor, or by affecting a component(s) of cellular biochemistry that directly or indirectly participates in the expression of the receptor. Alternatively, a modulator can act by accelerating or decelerating the turnover of the receptor either by direct interaction with the receptor or by interacting with another component(s) of cellular biochemistry which directly or indirectly effects the change.

A "polynucleotide" is a nucleic acid of more than one nucleotide. A polynucleotide can be made up of multiple polynucleotide units that are referred to by description of the unit. For example, a polynucleotide can comprise within its bounds a polynucleotide(s) having a coding sequence(s), a polynucleotide(s) that is a regulatory region(s) and/or other polynucleotide units commonly used in the art.

A "regulatory region" is a polynucleotide that can promote or enhance the initiation or termination of transcription or translation of a coding sequence. A regulatory region includes a sequence that is recognized by the RNA polymerase, ribosome, or associated transcription or translation initiation or termination factors of a host cell. Regulatory regions that direct the initiation of transcription or translation can direct constitutive or inducible expression of a coding sequence.

The isolated nucleic acid molecule of the present invention can include a deoxyribonucleic acid molecule (DNA), such as genomic DNA and complementary DNA (cDNA), which can be single (coding or noncoding) strand or double stranded, as well as synthetic DNA, such as a synthesized, single stranded polynucleotide. The isolated nucleic acid molecule of the present invention can also include a ribonucleic acid molecule (RNA).

The present invention also relates to recombinant vectors and recombinant hosts, both prokaryotic and eukaryotic, which contain the substantially purified nucleic acid molecules disclosed in this specification. Thus, the present invention relates to "expression systems", used herein to refer to a genetic sequence which includes a protein-encoding region and is operably linked to all of the genetic signals necessary to achieve expression of that region. Optionally the expression system may also include a regulatory element such as a promoter or enhancer, to increase transcription and/or translation of the protein-encoding region or to provide control over expression. The regulatory element may be located upstream or downstream of the protein-encoding region or within the protein-encoding region itself.

An "expression vector" is a polynucleotide having regulatory regions operably linked to a coding region such that, when in a host cell, the vector can direct the expression of the coding sequence. Expression vectors are DNA sequences that are required for the transcription of cloned DNA and the translation of their mRNA's in an appropriate host. Such vectors can be used to express eukaryotic DNA in a variety of hosts such as bacteria, blue-green algae, plant cells, insect cells and animal cells. Specifically designed vectors allow the shuttling of DNA between hosts such as bacteria-yeast or bacteria-animal cells. An "appropriately constructed" expression vector should contain: an origin of replication for autonomous replication in host cells, selectable markers, a limited number of useful restriction enzyme sites, a potential for high copy number, and active promoters. The use of expression vectors is well known in the art. Expression vectors can be used in a variety of host cells and, therefore, the regulatory regions are preferably chosen as appropriate for the particular host cell.

As used herein, a "promoter" is a DNA sequence that directs RNA polymerase to bind to DNA and initiate RNA synthesis. A "strong" promoter is one which causes mRNA's to be initiated at high frequency. There are various commercially available mammalian, bacterial, fungal, and insect expression vectors for expression of the lamprey GnRH receptor in mammalian, bacterial, fungal, and insect cells respectively.

An expression vector containing DNA encoding the lamprey GnRH receptor can be used for expression of the lamprey GnRH receptor in a recombinant host cell. "Recombinant host cells" can be prokaryotic or eukaryotic, including, but not limited to, bacteria (such as E. coli); fungal cells (such as yeast); mammalian cells, including but not limited to, cell lines of human, bovine, porcine, monkey, and rodent origin; and insect cells.

An expression vector can be introduced into host cells via any of a number of known techniques, including but not limited to, transformation, transfection, protoplast fusion, and electroporation. The expression vector-containing cells are then individually analyzed to determine whether they produce the desired product (which in this case would be lamprey GnRH receptor). Identification, in this case, of lamprey GnRH receptor-expressing cells can be done by several known means, including, but not limited to immunological reactivity with anti-lamprey GnRH antibodies, labeled ligand binding, and the presence of host cell-associated GnRH activity.

Cloned receptor cDNA obtained through the methods described above could be recombinantly expressed by molecular cloning into an expression vector containing a suitable promotor and other appropriate transcription regulatory elements, and transferred into prokaryotic or eukaryotic host cells to produce recombinant lamprey GnRH receptor. Techniques for such manipulation are well known and easily available to one of ordinary skill in the art.

Polynucleotides of the invention contain full length or partial length sequences of the receptor gene. Polynucleotides of the invention can be single or double stranded. If single stranded, the polynucleotides can be a coding, "sense", strand or a complementary, "antisense", strand. Antisense strands can be useful as modulators of the receptor by interacting with RNA encoding the receptor. Antisense strands are preferably less than full-length strands having sequences unique or highly specific for RNA encoding the receptor.

The polynucleotides of the invention can include deoxyribonucleotides, ribonucleotides or mixtures of both. The polynucleotides can be produced by host cells, in cell-free biochemical reactions or through chemical synthesis. Non-natural or modified nucleotides can be present. Natural phosphodiester internucleotide linkages can be appropriate. However, polynucleotides can have non-natural linkages between the nucleotides. Non-natural linkages are well known in the art. "Peptide Nucleic Acid" (PNA) can also be used and resists degradation by nucleases. These linkages can be mixed in a polynucleotide.

"Purified" and "isolated" are used interchangeably herein to stand for the proposition that the polynucleotide(s), protein(s) and polypeptide(s), or respective fragment(s) thereof in question has been removed from its in vivo environment so that it can be manipulated by the skilled artisan, such as, but not limited to, sequencing, restriction digestion, site-directed mutagenesis, and subcloning into expression vectors for a nucleic acid fragment, as well as obtaining the protein or protein fragment in pure quantities so as to afford the opportunity to generate polyclonal antibodies, monoclonal antibodies, amino acid sequencing and peptide digestion. Therefore, the nucleic acids disclosed herein can be present in whole cells or in cell lysates or in a partially purified or substantially purified form. A polynucleotide is considered "purified" when it is purified away from environmental contaminants. Thus, a polynucleotide isolated from cells is considered to be "substantially purified" when purified from cellular components by standard methods, while a chemically synthesized nucleic acid sequence is considered to be "substantially" purified when purified from its chemical precursors.

As used herein, "antibody" includes not only monoclonal and polyclonal antibodies, but also antigen binding fragments thereof, trimeric or tetrameric constructs and recombinant or proteolytic antibody fragments. The Type-II receptor of the invention can be expressed and used to screen agents of potential therapeutic interest.

In addition, it is known that there is a substantial amount of redundancy in the various codons which code for specific amino acids. Therefore, the invention also includes those DNA sequences that encode RNA comprising alternative codons which code for the eventual translation of the identical amino acid of the receptor of the invention. Such varied codons include:

A=Ala=Alanine: codons GCA, GCC, GCG, GCU
C=Cys=Cysteine: codons UGC, UGU
D=Asp=Aspartic acid: codons GAC, GAU
E=Glu=Glutamic acid: codons GAA, GAG
F=Phe=Phenylalanine: codons UUC, UUU
G=Gly=Glycine: codons GGA, GGC, GGG, GGU
H=His=Histidine: codons CAC, CAU
I=Ile=Isoleucine: codons AUA, AUC, AUU
K=Lys=Lysine: codons AAA, AAG
L=Leu=Leucine: codons UUA, UUG, CUA, CUC, CUG, CUU
M=Met=Methionine: codon AUG
N=Asp=Asparagine: codons AAC, AAU
P=Pro=Proline: codons CCA, CCC, CCG, CCU
Q=Gln=Glutamine: codons CAA, CAG
R=Arg=Arginine: codons AGA, AGG, CGA, CGC, CGG, CGU
S=Ser=Serine: codons AGC, AGU, UCA, UCC, UCG, UCU
T=Thr=Threonine: codons ACA, ACC, ACG, ACU
V=Val=Valine: codons GUA, GUC, GUG, GUU
W=Trp=Tryptophan: codon UGG
Y=Tyr=Tyrosine: codons UAC, UAU.

Therefore, the present invention discloses codon redundancy which can result in differing DNA molecules expressing an identical protein. For purposes of this specification, a sequence bearing one or more replaced codons will be defined as a "degenerate variation". Also included within the scope of the invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide.

It is also known that DNA sequences coding for a peptide can be altered so as to code for a peptide having properties that are different than those of the naturally occurring peptide. Methods of altering DNA sequences include, but are not limited to, site directed mutagenesis. Examples of altered properties include, but are not limited to, changes in the affinity of an enzyme for a substrate or a receptor for a ligand.

When used herein, a "biologically active equivalent" or "functional derivative" of a wild type GnRH receptor possesses a biological activity that is substantially similar to the biological activity of the wild type receptor. The term "functional derivative" includes "fragments", "mutants", "variants", "degenerative variants", "analogs", and "homologues" or "chemical derivatives" of the wild type receptor. The term "fragment" refers to any polypeptide subset of wild type receptor. The term "mutant" refers to a molecule that may be substantially similar to the wild type form but possesses distinguishing biological characteristics. Such altered characteristics include, but are not limited to, altered substrate binding, altered substrate affinity and altered sensitivity to chemical compounds affecting biological activity of the receptor or receptor functional derivative. The term "variant" refers to a molecule substantially similar in structure and function to either the entire wild type protein or to a fragment thereof. A molecule is "substantially similar" to a wild type receptor if both molecules have substantially similar structures or if both molecules possess similar biological activity. Therefore, if the two molecules possess substantially similar activity, they are considered to be variants even if the structure of one of the molecules is not found in the other or even if the two amino acid sequences are not identical. The term "analog" refers to a molecule substantially similar in function to either the full length receptor or to a biologically active fragment thereof.

A protein or fragment thereof is considered "purified or isolated" when it is obtained at a concentration at least about five-fold to about ten-fold higher than that found in nature. A protein or fragment thereof is considered "substantially pure" if it is obtained at a concentration of at least about 100-fold higher than that found in nature. A protein or fragment thereof is considered "essentially pure" if it is obtained at a concentration of at least about 1000-fold higher than that found in nature.

As used herein, "riboprobes" are RNA hybridization probes.

When referred to herein, "probes", including "riboprobes" can be labeled any number of ways known in the art, including, but not limited to, isotopes, enzymes, substrates, chemiluminescent, electrochemiluminescent, biotin, and fret pairs. A labeled probe can generate signal directly (isotopes), upon hybridization (fret pairs), indirectly after a chemical (luminescence) or biological (enzyme-substrate) reaction, or after binding a strepavidin-linked moiety that can generate a detectable signal directly or indirectly. Labeling of probes and generation of detectable signals are well-known techniques in the art and include, but are not limited to, Polymerase Chain Reaction and Reverse Transcriptase Polymerase Chain Reaction (PCR and RT-PCR), Strand Displacement Amplification, Self-Sustained Sequence Reaction and any other amplification technique known in the art that uses primers.

Results

Thus, according to the invention, a 1,838-base full-length cDNA encoding a putative GnRH receptor has been identified from sea lamprey by Applicants. This transcript sequence includes a 54-base 5'-untranslated region; a 1,380-base reading frame (coding region); and a 404-base 3'-untranslated region. The transcript encodes a fully functional seven transmembrane domain receptor protein of 460 amino acids.

Analysis of the encoded amino acid sequence showed maintenance of the characteristic motifs of GnRH receptors and high overall similarity to previously identified GnRH receptors. Analysis of the putative amino acid sequence also revealed that it contains four potential methionine start codons within the first 13 codons of the reading frame. While it is presently unknown which of these start codons is used, multiple start codons are not unusual in GnRH receptor transcripts. The various translational start sites give N-terminal lengths of 49, 44, 39 and 37 amino acids respectively. The regional comparison of the transcript of the invention to known GnRH receptors demonstrates maintenance of the high sequence conservation of the transmembrane helices and of intracellular loop 2. The relatively low conservation of extracellular loop 3, the most crucial region of the receptor for ligand specificity was also maintained. The variations in the conserved GPCR motifs were also similar to other type-II GnRH receptors identified to date, as was the hydropathy plot of the predicted protein. The consistency of the transcript of the present invention with known functional GnRH receptors gives strong evidence of its functionality—i.e. that the peptide is able to bind type II GnRH.

Expression of the receptor transcript was demonstrated by RT-PCR in the proximal pars distalis and rostral pars distalis of the pituitary, as well as in the testes. Expression was visualized in the proximal pars distalis of the juvenile lamprey pituitary by in situ hybridization with digoxigenin-labeled riboprobes which are RNA hybridization probes. Differential regulation of receptor transcript by lamprey GnRH-III was demonstrated in the pituitary (up-regulation) and testes (down-regulation). The sequence, expression pattern, and transcriptional regulation of this receptor provide strong evidence for an ancestral type-II GnRH receptor that is likely involved in GnRH regulation of lamprey reproduction.

Applicants' putative GnRH receptor includes a C-terminal tail of 120 amino acids, which is the longest C-terminal end identified to date in a GnRH receptor. Since the description of the catfish GnRH receptor 1, the first identified GnRH receptor to retain the evolutionarily conserved intracellular C-terminal tail, it has become evident that the main structural difference within the GnRH receptor family is the presence or absence of the intracellular C-terminal tail.

As noted, there have not yet been any GnRH receptors isolated and cloned in earlier evolved vertebrates from Chondrichthyes or Agnatha. In the present invention, Applicants have isolated and characterized the cDNA precursor of a GnRH receptor from the sea lamprey pituitary. The transcript encodes a putative pituitary receptor that shares the characteristic transmembrane region motifs and hydropathic profile of GnRH receptors as well as a C-terminal tail of approximately 120 amino acids, considerably longer than any previously identified GnRH receptor. RT-PCR expression analysis showed detectable levels of this transcript in pituitary and testes, but not in brain. The putative amino acid sequence and the expression pattern of this GnRH receptor transcript suggest that it is representative of an ancestral GnRH receptor and that it likely plays a key role in regulation of reproduction in the sea lamprey.

Summary of Results of Lamprey GnRH RECEPTOR cDNA Isolation and Sequencing

Using PCR from genomic template with degenerate primers and subsequent 5' RACE from brain cDNA, a 1,838-base full-length cDNA (SEQ ID NO: 1) was identified and confirmed with at least three separate clones to each portion of the sequence. This transcript contains a 54-base 5' untranslated region (UTR), a 1,380-base coding region, and a 404-base 3' untranslated region (UTR). Translation of the coding region demonstrated that the identified transcript encoded a GnRH receptor sequence of 460 amino acids (SEQ ID NO: 2). Within this open reading frame, all of the expected regions of a functional GnRH receptor were identified, including a C-terminal intracellular tail of approximately 120 amino acids.

The putative lamprey GnRH receptor amino acid sequence was examined for conservation of the characteristic motifs of Class A GPCRs and of GnRH receptors. The putative lamprey GnRH receptor maintains all of the conserved motifs of Class A GPCRs with the exceptions characteristic of GnRH receptors. Based on this comparison, the lamprey GnRH receptor appears more closely related to type-II GnRH receptors than to type-I GnRH receptors.

The putative receptor amino acid sequence was compared to all previously identified GnRH receptors using MegAlign (Lasergene). The putative amino acid sequence encoded by the lamprey GnRH receptor transcript has high similarity to numerous GnRH receptors previously identified. It has highest similarity to those of the aquatic caecilian *Typhlonectes natans* (61.2%) (Ebersole, et al. unpublished, GenBank # AF174481), the amphibian *Rana catesbeiana* (60.7% and 59.8%), and the striped sea bass *Morone saxitilis* (59.6%).

EXAMPLES

Tissues

Adult sea lampreys, *Petromyzon marinus*, were collected at the Cocheco River fish ladder in Dover, N.H. These fish were maintained at the University of New Hampshire Anadromous Fish and Aquatic Invertebrate Research Lab (AFAIR Lab) according to UNH animal care guidelines. The animals were decapitated, immediately after which pituitary, brain, heart, liver, muscle, kidney, eye, and ovary/testes were dissected and frozen in liquid nitrogen. Pituitary was used for RNA isolation and cDNA synthesis, liver was used for genomic DNA isolation, and all tissues were used for RT-PCR expression studies.

Parasitic sea lampreys were obtained from the Hammond Bay Biological Station in Hammond Bay, Mich. These fish were maintained at the AFAIR lab according to UNH animal care guidelines. Fish were decapitated and their heads were dissected to expose the pituitary and brain for horizontal cryomicrotomy in preparation for in situ hybridization.

Lamprey Genomic DNA Isolation

Genomic DNA was isolated from 100mg of lamprey liver using the prescribed protocol from Sambrook and Russell, Section 6.7 (2001). This protocol was followed with the exception that the tissue was ground to a powder in liquid nitrogen using a mortar and pestle instead of being homogenized in a blender.

Total RNA Isolation

Total RNA was isolated from 1,000 lamprey pituitaries (approximately 1 gram) using Tri-Reagent (Molecular Research Center, Inc., Cincinnati, Ohio). This is a guanidinium thiocyanate-based method with subsequent chloroform: phenol extraction, as would be known in the art.

Poly $A^+$ RNA Isolation

Poly $A^+$ RNA was isolated from 10 μg (micrograms) lamprey pituitary total RNA using the protocol described by Sambrook and Russell, Section 7.13 (Sambrook and Russell, 2001). This protocol uses dT cellulose beads to isolate polyadenylated RNA.

PCR from Genomic DNA Template

PCR using lamprey genomic DNA as template was performed with degenerate primers designed to GnRH receptor transmembrane (™) regions 6 and 7. The sequences for these primers were provided to us by Dr. Brigitte Troskie (Troskie et al., 1998):

JH5s: 5'-CTCGAATTCGGNATHTGGTAYTGGT-3' (slightly modified from Troskie et al., 1998) (SEQ ID NO: 3); and

JH5α$_2$: 5'-ACACTCGAGCCRTADNTRNGGRTC-3'(SEQ ID NO: 4).

These oligos were obtained from OPERON.com. PCR reactions were mixed to total volume of 50 μL (microliter) [1× AMPLITAQ GOLD™ PCR buffer, 1 mM (milliM) dNTPs, 1.25 units AMPLITAQ DNA polymerase (all from PE BIO- SYSTEMS Foster City, Calif.), 2 µM (microM) each primer, 1 µL (microliter) DMSO, 4.35 µg (microgram) genomic DNA]. These reactions were cycled on an EPPENDORF PCR Gradient Thermocycler under the following conditions:
94° C. for 9 min.,
35 cycles of 93° C. for 1 min/53° C. for 2 min (10° C. gradient)/72° C. for 3 min,
72° C. for 5 mm.

PCR products were analyzed by agarose gel electrophoresis at 80 V for 1 hr and stained with ethidium bromide for visualization. When no product was visualized, 5 µL of PCR reaction were used as template for a second PCR reaction using the same conditions.

First Strand cDNA Construction

First strand cDNA was constructed using the 1$^{st}$ Strand cDNA Synthesis Kit from AMERSHAM PHARMACIA (Buckinghamshire, England, UK) with pituitary poly A$^+$ or total RNA as template. The cDNA construction was performed using the Not-I poly dT primer (Not1-dT$_{18}$)—the Not-I primer AAC TGG AAG AAT TCG CGG CCG CAG GAA (SEQ ID NO: 5) with the added poly T sequence TTT TTT TTT TTT TTT TTT (dT$_{18}$) (SEQ ID. NO: 6) for the first strand synthesis initiation. This first strand cDNA was then used as template for PCR with combinations of gene-specific primers, shown in Table 1 (SEQ ID NOS: 7-34), the degenerate JH5s and JH6α$_2$ primers, (SEQ ID NOS: 3 and 4) and the Not-I and Not-I poly dT reverse primers (SEQ ID NOS: 5 and 6).

Gene-Specific Primer Design

Gene specific primers (GSPs) were designed to the first and second group of positive clones acquired. The oligo toolkit at OPERON.com, Primer3 from the Whitehead Institute at the Massachusetts Institute of Technology, and DNASTAR (LASERGENE) were all used for primer design. The GSPs are shown below in TABLE 1 (SEQ ID NOS: 7-34)

TABLE 1

Lamprey GnRH Receptor Gene-Specific Primers: GSPs 2, 4, 6, 8, 10, 23, and 24 are 3' → 5' (antisense) primers, and all others are 5' → 3' (sense) primers. (SEQ ID NOS: 7-34)

| Primer | Sequence |
|---|---|
| 1GnRHrGSP1 | 5'-CGGAGCATTGTGTCACGCAAGGTCG-3' (SEQ. ID. NO. 7) |
| 1GnRHrGSP2 | 5'-CGACCTTGCGTGACACAATGCTCCG-3' (SEQ. ID. NO. 8) |
| 1GnRHrGSP3 | 5'-ATCCGTGTGATGGAGATTTGTGCCA-3' (SEQ. ID. NO. 9) |
| 1GnRHrGSP4 | 5'-TGGCACAAATCTCCATCACACGGAT-3' (SEQ. ID. NO. 10) |
| 1GnRHrGSP5 | 5'-CCGAACGCCAGCCACACAGGC-3' (SEQ. ID. NO. 11) |
| 1GnRHrGSP6 | 5'-GCCTGTGTGGCTGGCGTTCGG-3' (SEQ. ID. NO. 12) |
| 1GnRHrGSP7 | 5'-GCGGGCGAGTTCGTCTGCCG-3' (SEQ. ID. NO. 13) |
| 1GnRHrGSP8 | 5'-CGGCAGACGAACTCGCCCGC-3' (SEQ. ID. NO. 14) |
| 1GnRHrGSP9 | 5'-GGCTCGGCTCAAAGTGAATCCGCTG-3' (SEQ. ID. NO. 15) |

TABLE 1-continued

Lamprey GnRH Receptor Gene-Specific Primers: GSPs 2, 4, 6, 8, 10, 23, and 24 are 3' → 5' (antisense) primers, and all others are 5' → 3' (sense) primers. (SEQ ID NOS: 7-34)

| Primer | Sequence |
|---|---|
| 1GnRHrGSP10 | 5'-CAGCGGATTCACTTTGAGCCGAGCC-3' (SEQ. ID. NO. 16) |
| 1GnRHrGSP11 | 5'-AGCGTTCTGCTGGCGGTCCC-3' (SEQ. ID. NO. 17) |
| 1GnRHrGSP12 | 5'-TCACCCACGGCAACTTCGTCGAGCAG-3' (SEQ. ID. NO. 18) |
| 1GnRHrGSP13 | 5'-GCCCCTCCGAACGCCAGCCACACA-3' (SEQ. ID. NO. 19) |
| 1GnRHrGSP14 | 5'-GCCCCTGGACGCCGTGTGGCA-3' (SEQ. ID. NO. 20) |
| 1GnRHrGSP15 | 5'-CGGTCCCGCAGCTCTTTCTGTTCC-3' (SEQ. ID. NO. 21) |
| 1GnRHrGSP16 | 5'-CAAAAACTTCGTTCAGTGCGTCACCCACG-3' (SEQ. ID. NO. 22) |
| 1GnRHrGSP17 | 5'-TGGTATTGGTTCGACCGGAGCATTGTGTCACGC-3' (SEQ. ID. NO. 23) |
| 1GnRHrGSP18 | 5'-AACTTGACCGTGTTGTGCACCATCT-3' (SEQ. ID. NO. 24) |
| 1GnRHrGSP19 | 5'-GATCTCCAAGAGGATGCGAGAAGGA-3' (SEQ. ID. NO. 25) |
| 1GnRHrGSP20 | 5'-CAAAAACTTCGTTCAGTGCGTCACC-3' (SEQ. ID. NO. 26) |
| 1GnRHrGSP21 | 5'-TCTCCAAGAGGATGCGAGAAGGAAG-3' (SEQ. ID. NO. 27) |
| 1GnRHrGSP22 | 5'-CAAGAGGATGCGAGAAGGAAGCATT-3' (SEQ. ID. NO. 28) |
| 1GnRHrGSP23 | 5'-CCACCACTGGCATCACAGAACG-3' (SEQ. ID. NO. 29) |
| 1GnRHrGSP24 | 5'-GAGGCCGAGTAGCGAAAGGAGC-3' (SEQ. ID. NO. 30) |
| 1GnRHrGSP25 | 5'-GCCGCTGCTGCCGCTGGC-3' (SEQ. ID. NO. 31) |
| 1GnRHrGSP26 | 5'-CGTCACGGGCTCCTTTCGCTACTC-3' (SEQ. ID. NO. 32) |
| 1GnRHrGSP27 | 5'-CACGGGCTCCTTTCGCTACTCGGC-3' (SEQ. ID. NO. 33) |
| LGnRHrGSP28 | 5'-CGCAGTGTCTGCGTTATTCTCA-3' (SEQ. ID. NO. 34) |

Example 1

3' and 5'-Rapid Amplification of cDNA Ends (RACE)

Total RNA from lamprey pituitary was used to construct double-stranded cDNA using the Marathon cDNA Amplification Kit from CLONTECH (Palo Alto, Calif.). 3' and 5' RACE were performed using the gene-specific primers shown in TABLE 1 with the Marathon kit. Protocol prescribed for this system was followed using poly A$^+$ RNA isolated from lamprey pituitary/brain as 1$^{st}$ strand cDNA template or using first strand cDNA constructed from lamprey pituitary/brain total RNA using the method described above as template for ultimate second strand cDNA construction with the Marathon system. Control RACE reactions were optimized to the following thermocycles:

95° C. for 1 min,
5 cycles of 94° C. for 10 sec and 74° C. for 5 min,
5 cycles of 94° C. for 10 sec and 72° C. for 5 min,
10 cycles of 94° C. for 10 sec and 70° C. for 5 min, and
15 cycles of 94° C. for 10 sec and 68° C. for 5 min.

Experimental 3'- and 5'-RACE reactions were performed using various combinations of the above gene-specific primers and the Marathon adaptor primers. These combinations were used to amplify overlapping portions of the GnRH receptor cDNA. PCR products were subcloned and sequenced as described below.

Sub-Cloning

Clones were prepared for sequencing by standard TA-cloning with the pGEM T-easy Vector System (Madison, Wis.) (PROMEGA, Madison, Wis.), and inserts were sequenced at the Huntsman Cancer Institute DNA Sequencing Facility at the University of Utah. Sequences were analyzed using the LASERGENE DNASTAR suite of analysis programs. The full-length lamprey GnRH receptor cDNA was deposited in GenBank under accession number AF439802.

All PCR products visualized on agarose gel were subcloned using the following procedures:

PCR products were gel purified using the QIAEX II Gel Purification Kit and protocol from QIAGEN (Valencia, Calif.). Purified DNA clones were then ligated into pGEM T-easy vector using the pGEM T-easy Vector System from PROMEGA (Madison, Wis.). Reactions were prepared to a final volume of 10 µL (1× rapid ligation buffer, 3 µL purified DNA, 50 ng pGEM T-easy vector, 3 units T4 DNA ligase). Ligation reactions were incubated at room temperature for 1-2 hr or overnight at 4° C. Ligated plasmid was transformed into JM109 cells (PROMEGA). 4 µL of the ligation reaction were added to 25 µL of barely thawed JM109 cells in 1.5 mL eppendorf tubes and incubated on ice for 30 min. The reactions were then heat-shocked for 45 seconds at 42° C. and returned to ice for 2 min. 200 µL of SOC media were added and the cultures were incubated for 1.5 hr at 37° C. with shaking. Cultures were plated on LB/ampicillin (1.25 mg/plate). Plates were inoculated with 100 µL of a mixture of X-GAL (20 mg/mL) and IPTG prior to culture plating (0.05 M).

Plasmid Preparation

White colonies were picked from transformation plates and grown overnight at 37° C. in 3 mL LB/ampicillin (150 µg) with shaking. Overnight cultures were used for plasmid preparation with the Wizard Plus Miniprep (PROMEGA). The prescribed protocol was followed precisely for this procedure. 5 µL of purified plasmid were then digested with EcoRI in a final volume of 20 µL [2 µg BSA and 1× Multi-Core buffer (PROMEGA), 12 units EcoRI] at 37° C. for 1.5-2 hr. This digestion was analyzed by 1% agarose gel electrophoresis to ensure presence of expected clones and to quantitate the DNA for sequencing preparation. Samples were quantitated by comparison with the Low Mass DNA Ladder from GIBCO BRL (Grand Island, N.Y.).

DNA Sequencing

DNA sequencing was performed by The Huntsman Cancer Institute DNA Sequencing Facility at the University of Utah. This facility uses ABI automated fluorescent sequencers. Samples were submitted in 600 ng quantities mixed with 3.2 pmoles of primer in a total volume of 7 µL. Samples were sequenced using either the T7 or SP6 primer, as designated by the pGEM T-easy Vector System. Sequences were analyzed using the LASERGENE DNASTAR suite of analysis programs.

Results

Figure 1:
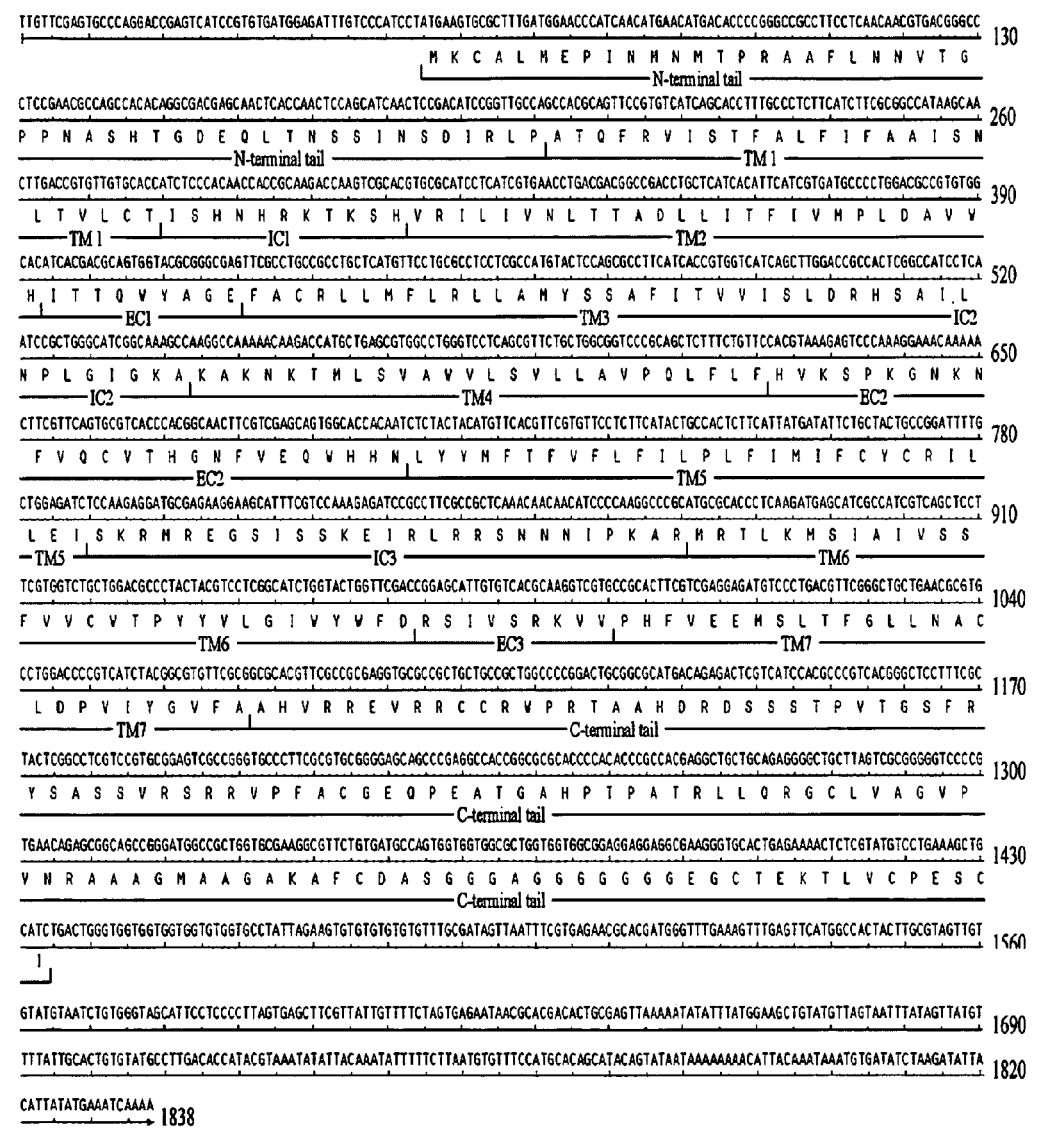

Using PCR from genomic template with degenerate primers and subsequent 5' RACE from brain cDNA, a 1,838-base full-length cDNA (SEQ ID NO: 1) was identified and confirmed with at least three separate clones to each portion of the sequence. This transcript contains a 54-base 5' untranslated region (UTR) (nucleotides 1-54), a 1,380-base coding region (reading frame) based on translation starting at the first AUG methionine codon (nucleotides 55-1434), and a 404-base 3' untranslated region (UTR) (nucleotides 1435-1838). Translation of the coding region demonstrated that the identified transcript encoded a GnRH receptor sequence of 460 amino acids (SEQ ID NO: 2). Within the open reading frame, all of the expected regions of a functional 7-TM GPCR (Trans-Membrane G Protein Coupled Receptor) were predicted and identified, as shown in FIG. 1, including a C-terminal intracellular tail of approximately 120 amino acids. The length, 120 amino acids, of this domain means that the lamprey GnRH receptor will be invaluable to understanding changes in receptor function with changes in intracellular tail length.

Analysis of the C-terminal tail indicated that the long C-terminal tail of the putative lamprey GnRH recpetor of the invention may function, in part, to produce the high levels of surface expression demonstrated in Applicants' previous GnRH binding studies. While the 1,380-base coding region identified was based on translation starting at the first AUG methionine codon, analysis of the putative lamprey receptor amino acid sequence revealed that it contains four potential methionine start codons within the first 13 codons of the reading frame. While it is unknown which one of these start codons is used, multiple start codons are not unusual in GnRH receptor transcripts. The various translational start sites give N-terminal lengths of 49, 44, 39 and 37 amino acids respectively. The regional comparison of the present transcript to other GnRH receptors demonstrates maintenance of the high sequence conservation of the transmembrane helices and of intracellular loop 2. The relatively low conservation of extracellular loop 3, the most crucial region of the receptor for ligand specificity was also maintained. The variations in the conserved GPCR motifs were also similar to other type-II GnRH receptors identified to date, as was the hydropathy plot of the predicted protein. The consistency of this transcript with known functional GnRH receptors gives strong evidence of its functionality.

Figure 3:
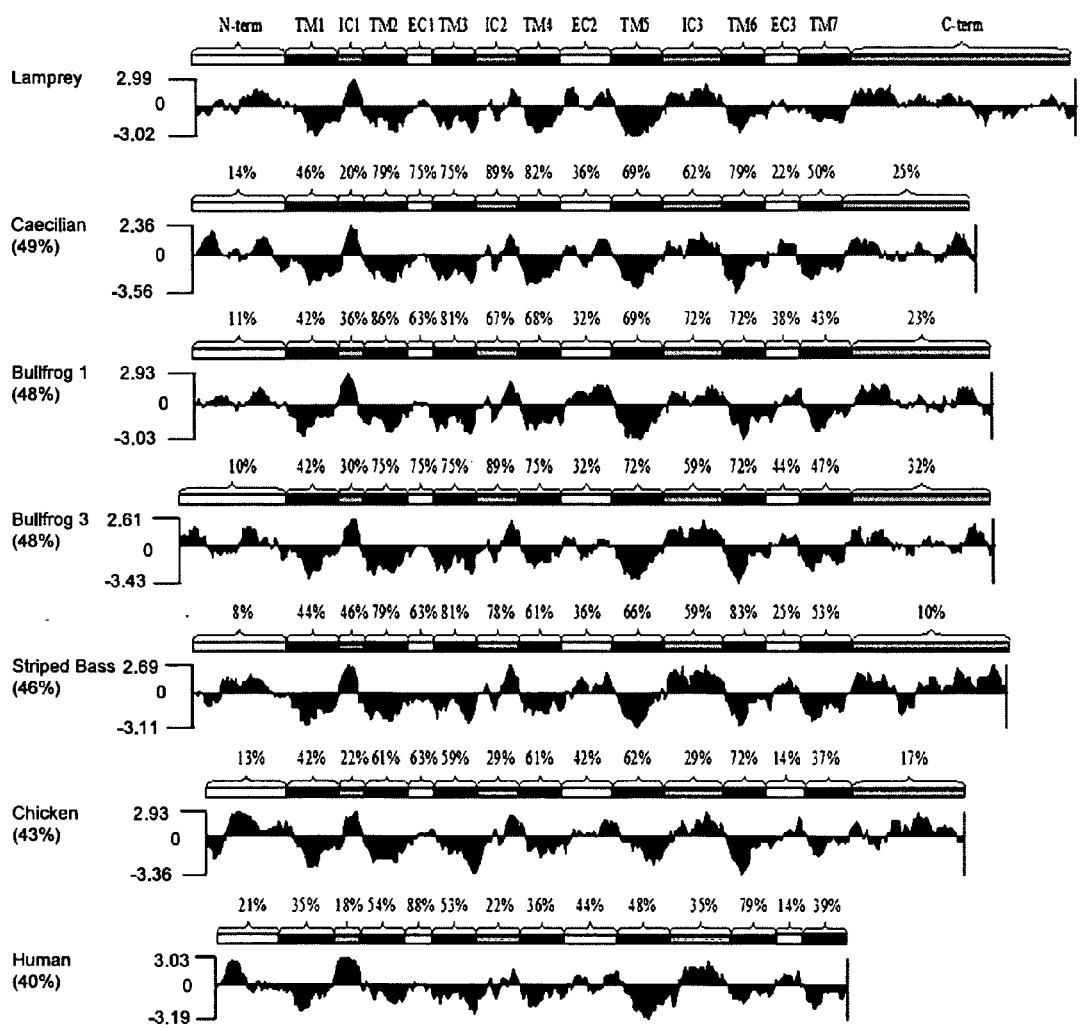
FIG. 3 shows regional and hydropathic comparison of lamprey GnRH receptor and representative GnRH-R's. Positive hydropathic values (peaks) indicate hydrophilicity, while negative hydropathic values (valleys) indicate hydrophobicity. The predicted receptor domains are indicated by: N-term=amino-terminal tail, IC=intracellular loop, TM=transmembrane domain, EC=extracellular loop, C-term=carboxyl-terminal tail. Percentages listed over each region represent percent amino acid identity of that region with the corresponding region of the predicted lamprey GnRH receptor protein. Overall identity with the lamprey receptor is shown under the organism name at left.

The putative amino acid sequence encoded by the lamprey GnRH receptor transcript has high identity to numerous GnRH receptors previously identified. See FIGS. 2 and 3 showing results of comparisons to previously identified receptors. The putative receptor amino acid sequence was compared to all previously identified GnRH receptors using MegAlign (LASERGENE). Applicants' receptor has highest similarity to those of the aquatic caecilian *Typhlonectes natans* (61.2%) (Ebersole, et al. unpublished)the amphibian bullfrog *Rana catesbeiana* (receptor 1:60.7% and receptor 2:59.8%), and the striped sea bass *Morone saxitilis* (59.6%). The chicken GnRH receptor and the human receptor were also used in this analysis and were found to have 43% and 40% identity, respectively. Protean (LASERGENE) was used to perform a Kyte-Doolittle hydrophilicity analysis of the amino acid sequence of the putative GnRH receptor, the results of which are shown in FIG. 3. This analysis revealed seven hydrophobic regions and an overall hydrophilicity plot very similar to those of other GnRH receptor amino acid sequences subjected to the same analysis.

In FIG. 2, shaded amino acids are shared with the consensus formed from the alignment (consensus not shown). Black bars above the sequence indicate transmembrane domains. And in FIG. 3, positive hydropathic values (peaks) indicate hydrophilicity, while negative hydropathic values (valleys) indicate hydrophobicity. The predicted receptor domains are indicated by: N-term=amino-terminal tail, IC=intracellular loop, TM=transmembrane domain, EC=extracellular loop, C-term=carboxyl-terminal tail. The percentages listed over each region represent percent amino acid identity of that region with the corresponding region of the predicted lamprey GnRH receptor protein. Overall identity with the lamprey receptor is shown under the organism name at left.

Figure 4:
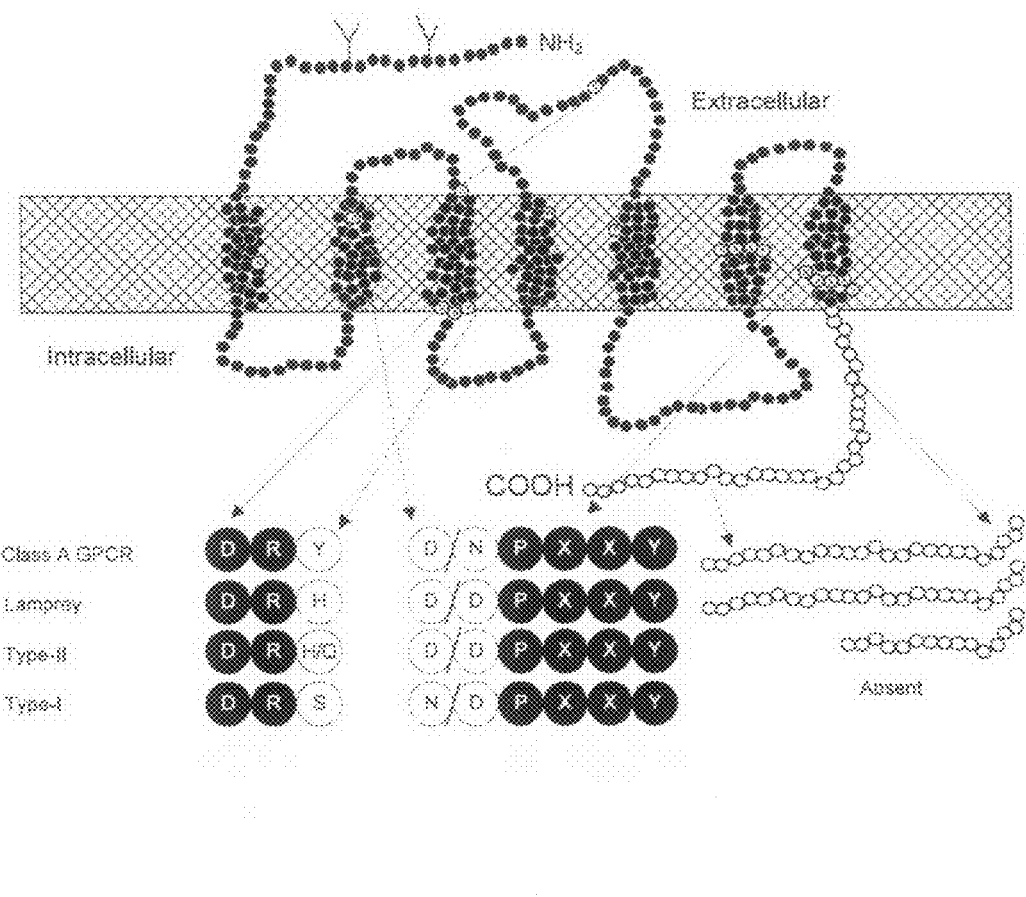
FIG. 4 shows the pattern of motif change through GnRH receptors. The conserved amino acid motifs of Class A GPCR's (G-protein coupled receptors) are shown in white with the conserved residue indicated. Three main motifs have changed significantly through GnRH receptor evolution. The tyrosine in TM3 has become variable, the aspartate/asparagines motif in TM2/7 has reversed, and the C-terminal tail has shortened to the point of non-existence in mammalian type I receptors.

The putative lamprey GnRH receptor amino acid sequence was also examined for conservation of the characteristic motifs of Class A GPCR's and of GnRH receptors, the results being shown in FIG. 4. The putative lamprey GnRH receptor of the invention maintains all of the conserved motifs of Class A GPCr's with the exceptions characteristic of GnRH receptors. Based on this comparison, the lamprey GnRH receptor of the invention appears more closely-related to type-II GnRH receptors that to type-I GnRH receptors. In the FIG., the conserved amino acid motifs of Class A GPCR's are shown in white with the conserved residue indicated. Three main motifs have changed significantly through GnRH receptor evolution. The tyrosine in TM 3 has become variable, the aspartate/asparagines motif in TM 2/7 has reversed, and the C-terminal tail has shortened to the point of non-existence in mammalian type I receptors.

Phylogenetic Analysis

Figure 5:
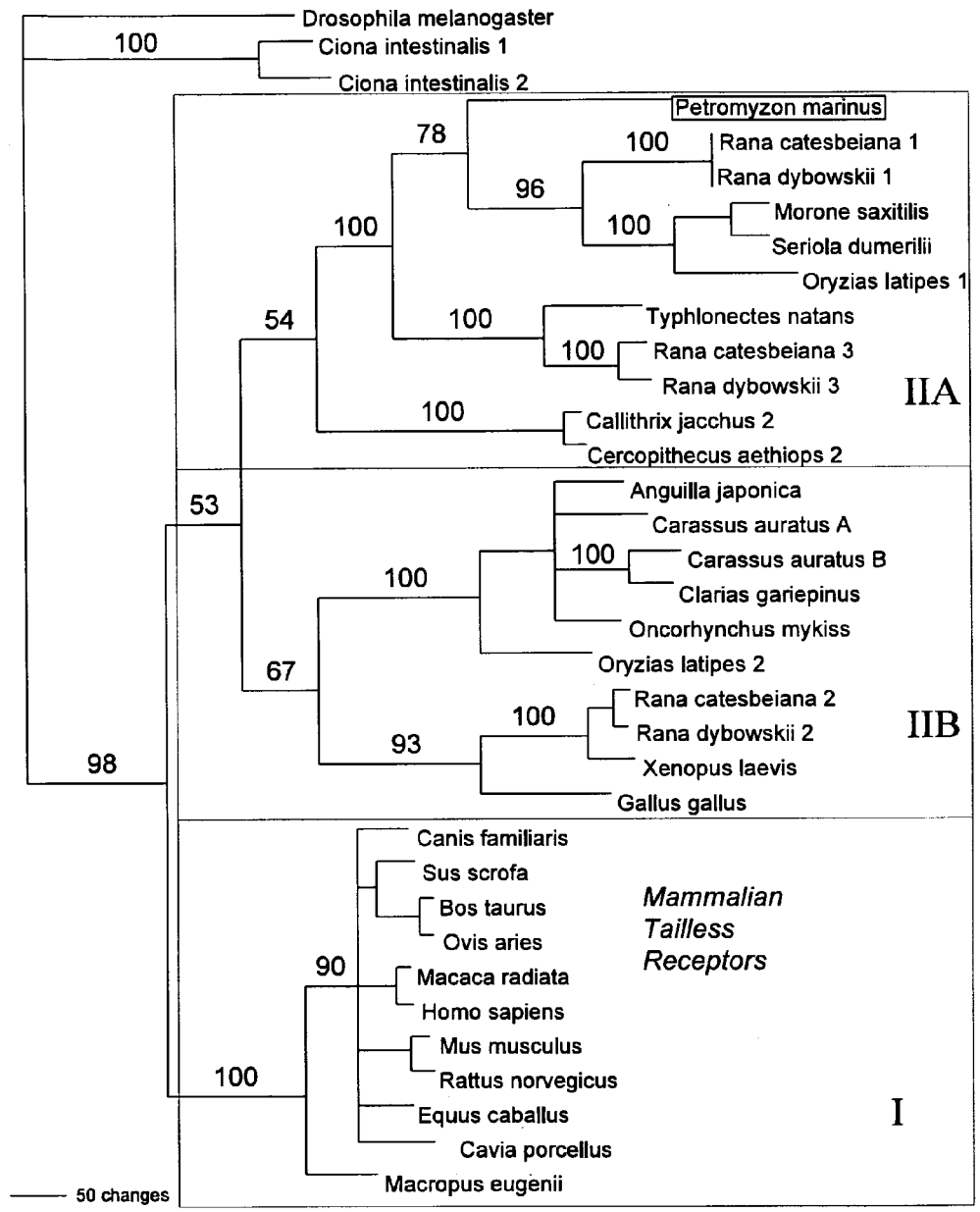
FIG. 5 shows the GnRH receptor phylogenetic tree. The GnRH receptor amino acid sequences group into three major clades, shown in light gray, gray and dark gray. The Drosophila receptor was designated as an outgroup, while the tunicate receptor sequences were outgrouped by the analysis. Applicants' revised classification is shown. Dark gray=Type IIA receptors, gray=Type IIB receptors; and light gray=Type I receptors.

Positive sequences were aligned by amino acid-coding sequence using the Clustal W method with MegAlign (Lasergene DNASTAR) to create a consensus sequence representing the lamprey GnRH receptor protein-coding sequence. This sequence was aligned, also using Clustal W, with 34 other known GnRH receptor amino acid sequences. This alignment was entered into PAUP (Phylogenetic Analysis Using Parsimony) 4.0 beta. Phylogenetic analysis was performed using maximum parsimony with heuristic tree construction and simple branch swapping. This method was used in a bootstrap search of 100 iterations; only branches with 50% frequency or better were retained. The results are shown in FIG. 5.

According to the analysis, the GnRH receptors grouped into three phylogenetic clades, shown in the FIG. in light gray, gray and dark gray, with the putative lamprey receptor grouping with type-II GnRH receptors from amphibians and mammals as well as with three fish receptors. The GnRH-like receptors identified in the fruit fly (*Drosophila melanogaster*) and tunicate form outgroups. The fruit fly receptor was designated as an outgroup, while the tunicate receptor sequences were outgrouped by the analysis. Applicants' revised classification is shown in FIG. 5. Dark gray=Type IIA receptors, gray=Type IIB receptors, and light gray=Type I receptors.

The sequences used were, and were obtained, as follows: *Mus musculus, Homo sapiens, Rattus norvegicus, Ovis aries, Bos Taurus, Sus scrofa, Macacca radiata, Canisfamiliaris, Equus caballus* (Proter et al., unpublished, GenBank # AF018072), *Cavia porcellus* (Fujii et al., unpublished, GenBank # AF426176), *Macropus eugenii, Drosophila melanogaster, Ciona intestinals* (Kusakabe et al., unpublished, GenBank # AB103333), *Seriola dumerilli* (Bogerd et al., unpublished, GenBank # AJ130876), *Typhlonectes natans* (Ebersole et al., unpublished, GenBank # AF174481), *Cercopithecus aethiops, Callithrix jacchus, Gallus gallus, Rana catesbeiana, Rana dybowskii, Xenopus laevis, Clarias gariepinus, Carassus auratus, Morone saxitillis, Oncorhynchus mykiss, Anguillajaponica,* and *Oryzias latipes.*

Example 2

Reverse-Transcriptase PCR

Total RNA was isolated and digested with DNase to remove any genomic remnants, and first strand cDNA was constructed from 100 mg each of lamprey brain, pituitary, heart, liver, muscle, eye, testes, ovary, and kidney using the above-described methods. The RNA stocks were then treated (1 µg/reaction) with RQ1 RNase-free DNase (PROMEGA), and 4 µl of each reaction was then used with the AccessQuick RT-PCR system (PROMEGA). LGnRHr GSP5 and 1GnRHr GSP 2 were used (2.5 pmol/reaction) with the following cycling parameters: 48° C. for 45 min; 95° C. for 2 min; 30 cycles of 95° C. for 15 sec, 68° C. for 1 min, 72° C. for 1 min; 72° C. for 5 min. Negative controls were performed by adding 1 µL of RNase (10 mg/mL) and incubating at 37° C. for 1 hour before adding AccessQuick reagents and cycling. Reaction products were analyzed using gel electrophoresis as described above. Receptor sequence was confirmed by subcloning and sequencing as described above.

Example 3

Tissue-Specific Expression

Reverse-Transcription PCR was performed using cDNA constructed from total RNA from lamprey brain, pituitary, ovary, testes, heart, muscle, liver, kidney, and eye. The targeted reaction product was amplified from pituitary, testes, and kidney. This technique demonstrates transcript presence but does not distinguish expression level or expression of partial or full-length transcript. The only tissue in which full-length transcripts have been isolated remains the pituitary.

Results

Figure 6:
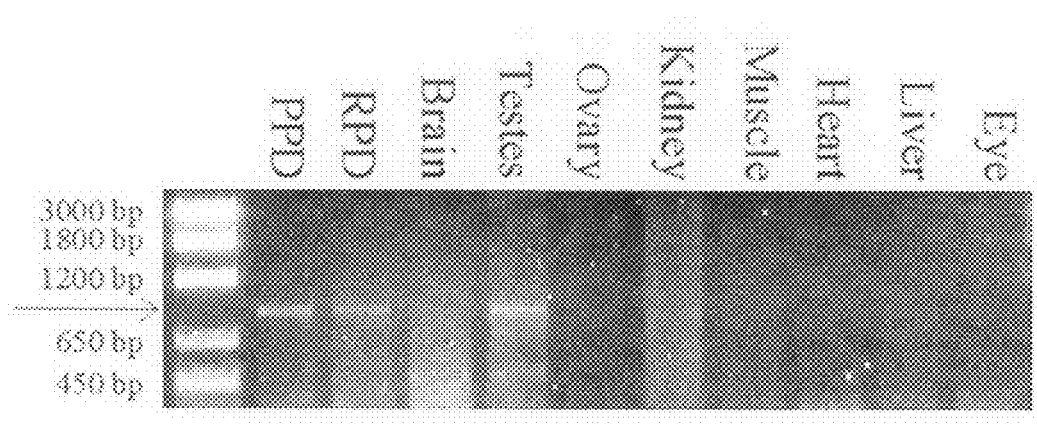
FIG. 6 shows the tissue-specific expression of the lamprey GnRH receptor transcript of the invention. The target product of approximately about 850 bases was produced in the proximal pars distalis, rostral pars distalis, and testes. Intensity of these bands was used for relative quantification.

The target sequence of approximately 840 bases was visualized in the pars intermedia, proximal pars distalis, rostral pars distalis, and testes, as shown in FIG. 6 following RT-PCR from lamprey proximal pars distalis, rostral pars distalis, brain, ovary, testes, heart, muscle, liver, kidney and eye. Intensity of the bands was used for relative quantitation. Expression appeared high in the proximal pars distalis and low in the rostral pars distalis and testes.

The visualization of the lamprey receptor transcript in multiple tissues implies that, like other type-II receptors, this receptor may have functions outside the pituitary in addition to binding to GnRH in the pituitary.

Example 4

Genomic GnRH Receptor Sequence Amplification

Parallel reactions, using the Advantage2 Taq Polymerase (CLONTECH) under the same concentrations and cycling parameters listed above for the 3' and 5' RACE experiments, were cycled with the RT-PCR reactions using RNase-digested genomic DNA template as a negative control. RNase-treated lamprey genomic DNA was used as template with five primer sets; forward primers GSP's 3, 5, 12, 14, and 15 (SEQ ID NOS: 7, 9, 16, 18, and 19) were used with the same reverse primer, GSP2 (SEQ ID NO: 6). Each of these primer sets spanned at least one conserved intron site. PCR from genomic DNA using primers to the 5' and 3' ends of the identified sequence yielded full-length sequence identical to that obtained from cDNA template.

Results

Figure 7:
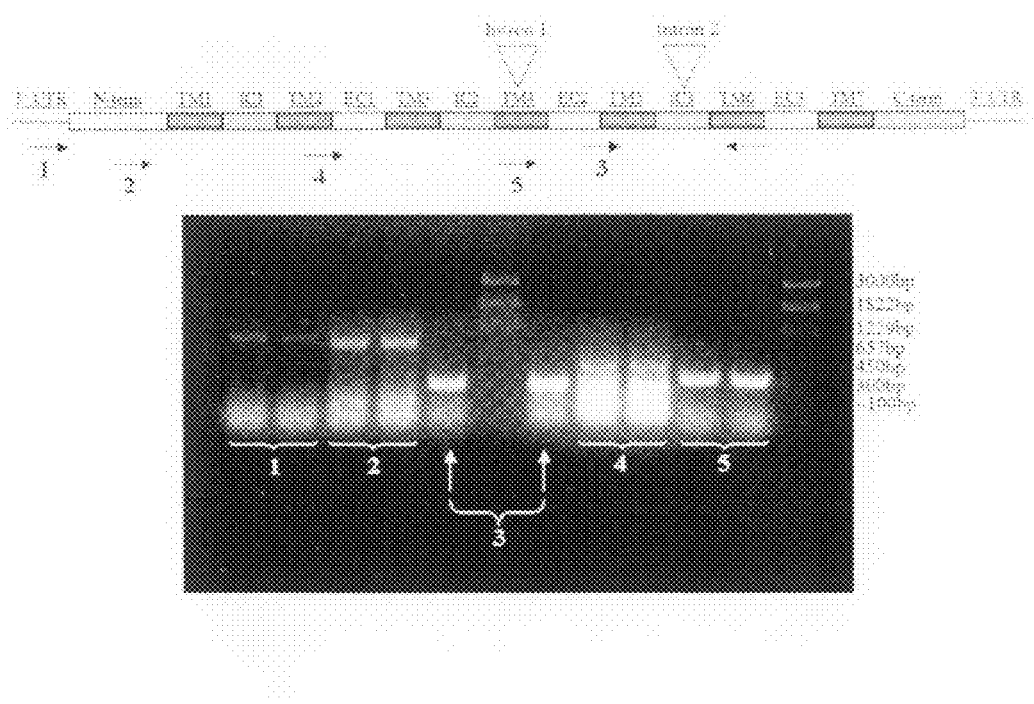
FIG. 7 shows an analysis of conserved introns. Arrows indicate positions of the primers used within the lamprey GnRH receptor coding sequence in PCR reactions from genomic template. Wedges designate conserved positions of introns, as shown in all previously characterized GnRH receptor genes. All five primer pairs produced the same amplimer from genomic DNA template as from cDNA template, indicating that the lamprey GnRH receptor gene lacks introns in the conserved positions.

All five primer sets produced the same product produced from pituitary cDNA template, as shown in FIG. 7. In FIG. 7, arrows indicate positions of the primers used within the lamprey GnRH receptor coding sequence in PCR reactions from genomic template. Wedges designate conserved positions of introns, as shown in all previously characterized GnRH receptor genes.

PCR from genomic DNA template using multiple primer sets yielded the same product as that identified from cDNA template with no introns from the 5' end of the transcript through the region encoding extracellular loop 3. These products were isolated and sequenced to demonstrate contiguous amplification of coding sequence through both conserved intron sites.

Because all five different primer sets, spanning one or both conserved intron sites produced identical products, this suggested that the GnRH receptor gene lacks introns in the conserved positions. This lack of introns in the conserved positions is unlike all previously described GnRH receptor genes. Further PCR was performed with primers to both ends of the identified sequence, and full length GnRH receptor sequence was isolated from genomic DNA, again suggesting a lack of the conserved introns seen in other GnRH receptors. The sequences of these clones were confirmed by subcloning and sequencing as described above. The lack of conserved introns in the present transcript provides evidence that it is representative of an ancestral GnRH receptor.

Example 5

In Situ Hybridization and Expression Mapping in the Brain and Pituitary

In situ hybridization was performed on horizontal sections of juvenile parasitic lamprey pituitaries and brains to map the expression level and localization of the GnRH receptor transcript. The GnRH receptor transcript was visualized in the proximal pars distalis of two lamprey pituitaries. No expression was visualized in the lamprey brain. This expression is seen in the same portion of the lamprey pituitary in which GnRH binding sites are known to be concentrated.

In situ hybridization was performed as described below, based on protocol of Dr. Beverly Rubin, Tufts Medical School with the following modifications. One variation used a 2-minute incubation in 0.1×SSC with 10 mM DTT instead of a 30-minute incubation.

In Situ Hybridization Probe Synthesis

Brain and pituitary were dissected from two parasitic lampreys and were oriented for horizontal sectioning. DNA fragments representing portions of the lamprey GnRH receptor transcript were produced by RT-PCR as described above. The GnRH-R probes were produced by reverse transcription of two PCR-amplified (GSP13 vs. GSP8 and GSP19 vs. GSP24) portions of the GnRH receptor transcript. These represent a 500-nucleotide sequence that includes the coding sequence from the extracellular end of transmembrane region 1 through the C-terminal end of extracellular loop 1 and a 336-nucleotide sequence corresponding to the coding region of intracellular loop 3 through the middle of the C-terminal tail. A mixture of these two probes was used (10.0 ng/µL of each). These segments were used in combination because a full-length probe would cause difficulties with labeling and tissue permeability.

Results

Figure 8:
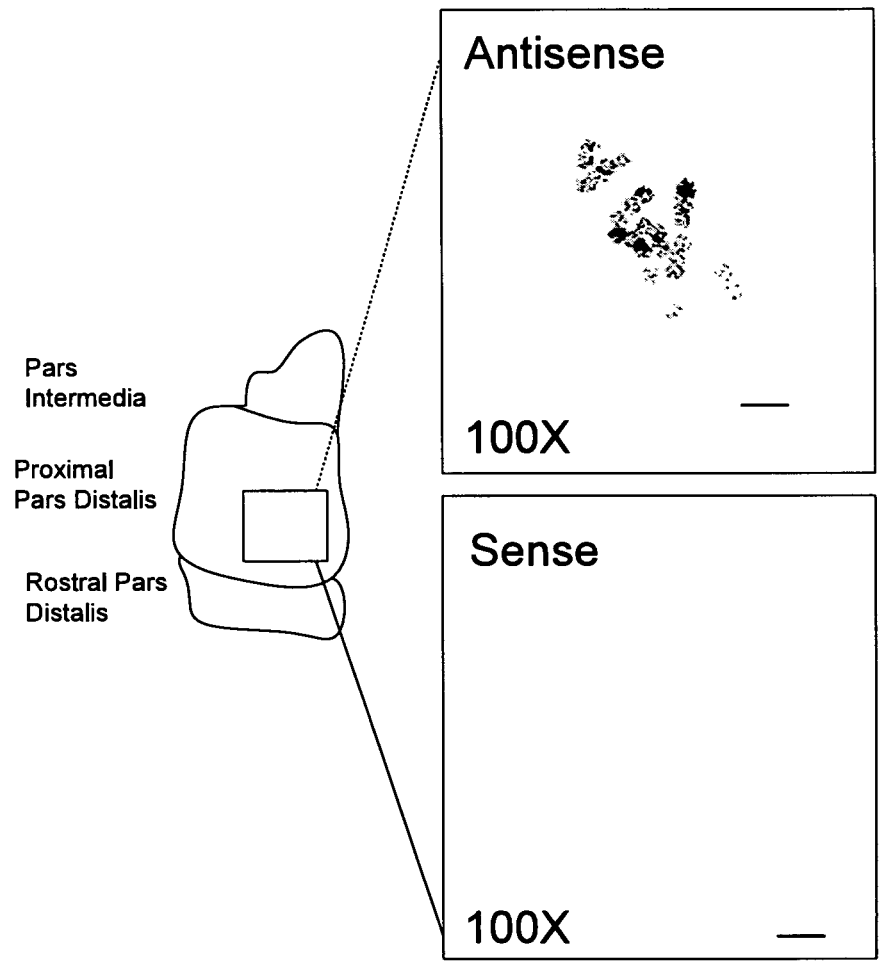
FIG. 8 shows results of in situ hybridization in the pituitary of a parasitic lamprey. Antisense probe showed expression of the lamprey GnRH receptor transcript in the proximal pars distalis of a parasitic lamprey pituitary. Sense probe in the same pituitary showed no staining. Bar=100 μm. This photomicrograph is representative of two (2) parasitic lampreys.

In situ hybridization with a specific riboprobe to the lamprey GnRH receptor showed moderate levels of expression in the proximal pars distalis of the pituitary. Expression of the receptor transcript was visualized in the proximal pars distalis of the juvenile lamprey pituitary (N=2), by in situ hybridization with digoxigenin-labeled riboprobes and the results are shown in FIG. 8. Antisense probe showed expression in the proximal pars distalis of a parasitic lamprey pituitary. Sense probe in the same pituitary showed no staining. Bar-100 µm. The photomicrograph of FIG. 8 is representative of two (2) parasitic lamprey. This expression is seen in the same portion of the lamprey pituitary in which GnRH binding sites are known to be concentrated. GnRH receptor transcript expression was not detected in the lamprey brain. Because of the limited availability of adult lamprey brains and pituitary, juvenile lampreys were used for the study.

Example 6

Transcriptional Regulation by Lamprey GnRH-III

Forty adult male lamprey's were injected intraperitoneally, twenty (20) with lamprey GnRH-III (200 µL of 0.45 µg/µL lamprey GnRH-III in 0.6% saline) and twenty (20) with control (200 µL of 0.6% saline). Ten (10) fish from each treatment group were sacrificed 24 hours after injection, and brains, pituitaries, kidneys, and testes were dissected and frozen in liquid nitrogen. Forty-eight hours after the first injection, the remaining animals were injected a second time with the same treatment they originally received. Twenty-four hours after the second injection, all remaining animals were sacrificed and tissues dissected and snap frozen. Total RNA was isolated from all tissues using Tri-Reagent (Molecular Research Center, Inc.), treated with RQ1 DNase (PROMEGA), and used as template for RT-PCR with the AccessQuick RT-PCR system (PROMEGA) using the same conditions as above, except 50 ng of template was used per reaction. Reactions were electrophoresed and visualized in 2% agarose gels. Parallel reactions were performed using primers to β-actin as a positive control. Receptor bands were normalized to β-actin and densitometry was performed using a Molecular Imager FX (Bio-Rad, Hercules, Calif.) to determine effects of lamprey GnRH-III injection.

Results

It has been well established that GnRH regulates expression of its own receptor. Pulsatile GnRH exposure generally causes up-regulation of pituitary receptors, while static GnRH exposure causes down-regulation. Applicants' previous studies have demonstrated that lamprey physiological responses to GnRH are increased with multiple injections of GnRH. These results were presumed to be due to an upregulation of GnRH receptors upon GnRH treatment. Herein, Applicants provide the first data directly supporting a mechanism of GnRH control over its pituitary receptors in the lamprey.

The GnRH receptor transcript of the invention is strongly up-regulated in the pituitary by lamprey GnRH-III and strongly down-regulated in the testes, though additional analyses are necessary to ensure that this regulation is carried through in expression of the active receptor protein. These data suggest an important interplay between lamprey GnRH- III and the present transcript, an interplay that indicates that this transcript likely produces a physiologically important receptor.

Figure 9:
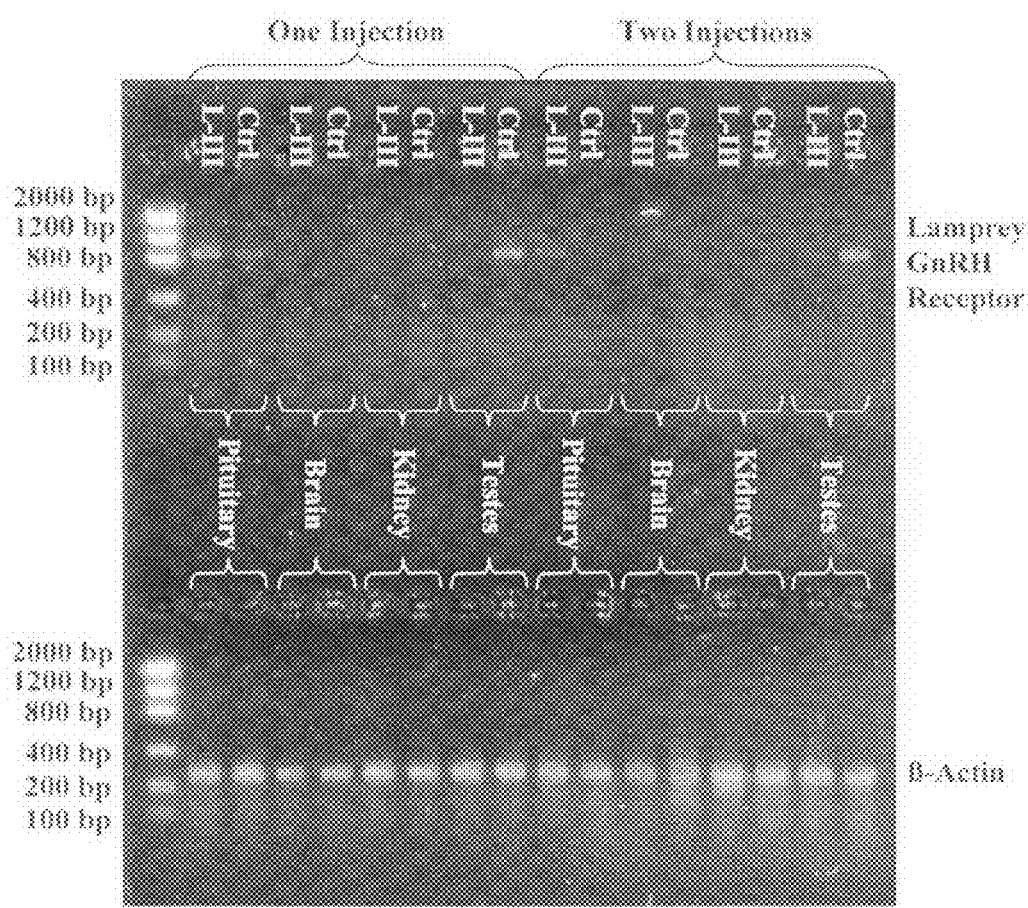
FIG. 9 shows the transcriptional regulation of the lamprey GnRH receptor transcript by lamprey GnRH-III. The target product of approximately about 850 bases was amplified in pituitary and testes of fish treated once (left) and twice (right) with lamprey GnRH-III or control, as indicated. Brain expression was not induced by lamprey GnRH-III. Kidney was included as a negative control. B-actin was amplified from every tissue sampled and used for normalization. The intensities of the receptor bands in this image are representative of the relative values after this normalization, as calculated by densitometry.

In response to lamprey GnRH-III treatment, receptor transcript was up-regulated in the pituitary and down-regulated in the testes after both one and two injections of lamprey GnRH-III, as compared to control, based on densitometry performed after normalization to β-actin (N=10), as shown in FIG. 9. The target product of approximately 850 bases were amplified in pituitary and testes of fish treated once (left) and twice (right) with lamprey GnRH-III or control, as indicated in the FIG. Brain expression was not induced by lamprey GnRH-III. Kidney was included as a negative control. B-actin was amplified from every tissue sampled and used for normalization. The intensities of the receptor bands in FIG. 9 are representative of the relative values after this normalization as calculated by densitometry.

After one injection, receptor transcript bands from lamprey GnRH-III-injected pituitary were twice as bright as control while GnRH receptor transcript went from high levels in the control testes to barely detectable levels in the lamprey GnRH-III-injected testes. The same effects were seen after two injections, although to a considerably lesser degree. No expression was detected in the brain or kidney (negative control) after either injection. For this study, total RNA from each tissue from each sample group was run in RT-PCR reactions in triplicate. FIG. 9 is representative of results seen in each of the three reaction trials.

Example 7

The cloned receptor was shown to encode a functional product as determined by both inositol phosphate (IP) and cAMP assays, in which stimulation of transiently transfected COS7 cells with either lamprey GnRH-I or lamprey GnRH-III led to dose dependant responses. RT-PCR expression analysis has shown detectable levels of this transcript in pituitary and testes, but not in brain. The putative amino acid sequence and the expression pattern of this GnRH receptor transcript suggest that it is representative of an ancestral GnRH receptor and that it likely plays a key role in regulation of reproduction in the sea lamprey.

Tissues

Adult sea lampreys, Petromyzon marinus, were collected at the Cocheco River fish ladder in Dover, N.H. These fish were maintained at the University of New Hampshire Anadromous Fish and Aquatic Invertebrate Research Lab (AFAIR Lab) in accordance with UNH animal care guidelines. The animals were decapitated, immediately after which pituitary, brain, heart, liver, muscle, kidney, eye, and ovary/testes were dissected and frozen in liquid nitrogen. Pituitary was used for RNA isolation and cDNA synthesis, liver was used for genomic DNA isolation, and all tissues were used for RT-PCR expression studies. Parasitic sea lampreys were obtained from the Hammond Bay Biological Station in Hammond Bay, Mich. These fish were sent to UNH and maintained at the AFAIR lab in accordance with UNH animal care guidelines. Fish were decapitated and their heads were dissected to expose the pituitary and brain for horizontal cryomicrotomy in preparation for in situ hybridization.

Nucleotide Isolation

Genomic DNA was isolated from 100 mg of lamprey liver using the prescribed protocol from Sambrook and Russell, Section 6.7 (25). Total RNA was isolated from 1,000 lamprey pituitaries (approximately 1 gram) using Tri-Reagent (Molecular Research Center, Inc., Cincinnati, Ohio), per the manufacturers guidelines. PCR from Genomic DNA template Lamprey genomic DNA was used as template for PCR with degenerate primers designed to GnRH receptor transmembrane (™) regions 6 and 7. The sequences for these primers were provided by Dr. Brigitte Troskie (26): JH5s: 5-CTCGAATTCGGNATHTGGTAYTGGT-3 (SEQ ID NO: 3) JH6±2: 5-ACACTCGAGCCRTADATNTRNGGRTC-3 (SEQ ID NO: 35).

These oligos were obtained from OPERON.com. Reactions were mixed to total volume of 50° L [1× Amplitaq Gold™ PCR buffer, 1 mM dNTPs, 1.25 units Amplitaq DNA polymerase (all from PE Biosystems, Foster City, Calif.), 2 µM each primer, 1 µL DMSO, 4.35 µg genomic DNA]. These reactions were cycled on an Eppendorf PCR Gradient Thermocycler under the following conditions: 94° C. for 9 min.; 35 cycles of 93° C. for 1 min, 53° C. for 2 min, 72° C. for 3 min, 72° C. for 5 min.

First Strand cDNA Construction

First strand cDNA was constructed using the 1st Strand cDNA Synthesis Kit from AMERSHAM-PHARMACIA (Buckinghamshire, England, UK) from pituitary total RNA with the NotIdT18 primer. This first strand cDNA was then used as template for PCR with combinations of gene-specific primers (See Table 1), the degenerate JH5s and JH6±2 primers, and the Not-I and poly dT reverse primers. 3 and 5-Rapid Amplification of cDNA Ends (RACE). Total RNA from lamprey pituitary was used to construct double-stranded cDNA using the Marathon cDNA Amplification Kit (CLONTECH, Palo Alto, Calif.). 3 and 5 RACE were performed with this system using various gene-specific primers (Integrated DNA Technologies, Coralville, Iowa) (Table 1). RACE reactions were performed with the following parameters: 95° C. for 1 min, 5 cycles of 94° C. for 10 sec and 74° C. for 5 min, 5 cycles of 94° C. for 10 sec and 72° C. for 5 min, 10 cycles of 94° C. for 10 sec and 70° C. for 5 min, 15 cycles of 94° C. for 10 sec and 68° C. for 5 min. Experimental 3- and 5-RACE reactions were performed using various combinations of the above gene specific primers and the Marathon adaptor primers. These combinations were used to amplify overlapping portions of the GnRH receptor cDNA. Clones were prepared for sequencing by standard TA-cloning with the pGEM T-easy Vector System(PROMEGA, Madison, Wis.), and inserts were sequenced at the Huntsman Cancer Institute DNA Sequencing Facility at the University of Utah. Sequences were analyzed using the LASERGENE DNA STAR suite of analysis programs. The full-length lamprey GnRH receptor cDNA was deposited in GenBank under accession number AF439802.

Cell Culture and Transfection

The coding region of the lamprey GnRH-R was inserted into the pcDNA3.1 HisTOPO mammalian expression vector (Carlsbad, Calif.). (INVITROGEN, Carlsbad, Calif.) COS7 cells were cultured in 10% fetal bovine serum (FBS) in Dulbeccos Modified Eagles Medium (DMEM) (INVITROGEN), and were maintained at 37° C. in 5% CO 2. The day before transfection, 5×10 5 cells were seeded in 60 mm culture plates. Transfection was performed using 5 µg of vector and 15 µL of Lipofectamine (INVITROGEN) in 2.4 mL total volume in Opti-MEM-I (INVITROGEN) and an incubation time of 5 hours at 37° C. in 5% CO 2, after which, 2.5 mL of 20% FBS in DMEM was added and cultures were grown overnight.

cAMP Assay

Twenty-four hours after transfection (day 2), cells were trypsinized and 96-well plates were seeded with 5×10 4 cells/ well, and cultures were grown overnight. Day 3, cells were stimulated with either control (ID buffer—1.0 mM 3-isobu-tyl-1-methylxanthine in DMEM) or varying concentrations (10-10M to 10-4M) of either lamprey GnRH-I or lamprey GnRH-III (in ID buffer). cAMP assays were performed using the BIOTRAK Enzymeimmunoassay system (AMERSHAM), per the manufacturers instructions. Treatments were performed in triplicate in three independent experiments, while cells transfected with blank vector were used as negative controls. Analyses were performed using GRAPHPAD (Prism, San Diego, Calif.). Inositol Phosphate Assay The inositol phosphate (IP) stimulation and extraction protocol used was adapted from previous studies. Briefly, 24 hours after transfection, cells were trypsinized, and seeded in 12-well plates at approximately 1.5×10 5 cells/well. At hour 72 cells were washed in PBS and incubated in 1 mL of 2% dialyzed fetal bovine serum and 2 µCi/mL myo [23H] inositol (AMERSHAM) in medium 199 (INVITROGEN). At hour 96 cells were washed 2 times with IP buffer (1×HBSS, 20 mM HEPES, 20 mM LiCL), and were pre-incubated in IP buffer for 15 minutes at 37° C., followed by stimulation with concentrations of lamprey GnRH-I or lamprey GnRH III, in IP buffer, ranging from 10-6M to 10-11 M, for 1 hour at 37° C. with gentle shaking. The reactions were stopped with the addition of 0.2 mL of pre-chilled 20% perchloric acid, and the plates were placed on ice for 30 minutes. The wells were scraped and the extracts were transferred to sterile 1.5 mL tubes and neutralized with 5M KOH, followed by a 1 hour incubation at 4° C. Tubes were centrifuged at 5,000 rpm at 4° C. for 15 minutes, and 1.2 mL of supernatant was transferred to a new sterile 1.5 mL tube. EPs (IP, IP2 and IP3) were isolated by ion exchange chromatography using AG1X8-200 resin (Bio-Rad) in formate form. IPs were eluted with 1 M ammonium formate/0.1 M formic acid, samples were counted by liquid scintillation and data were analyzed using Prism (GRAPHPAD). Treatments were performed in triplicate in three independent experiments, and cells transfected with blank vector and non-transfected cells were used as negative controls.

Phylogenetic Analysis

Positive sequences were aligned by amino acid-coding sequence using the ClustalW method with MegAlign (LASERGENE DNASTAR) to create a consensus sequence representing the lamprey GnRH receptor protein-coding sequence. This sequence was aligned, using ClustalV, with 36 other known GnRH receptor amino acid sequences and analyzed using PAUP (Phylogenetic Analysis Using Parsimony) 4.0 beta10. Trees were constructed using a neighbor joining analysis with 1000 bootstrap replicates; only branches with 50% frequency or better were retained.

Reverse Transcriptase PCR

Total RNA was isolated from the pars intermedia, proximal pars distalis, rostral pars distalis, brain, heart, liver, muscle, eye, testes, ovary, and kidney using Tri-Reagent (Molecular Research Center, Inc.). These RNA stocks were then treated (1 µg/reaction) with RQ1 RNasefree DNase (PROMEGA), and 4 µl of each reaction was then used with the AccessQuick RT-PCR system (promega). (PROMEGA). LGnRHr GSP5 and 1GnRHr GSP2 were used (2.5 pmol/reaction) with the following cycling parameters: 48° C. for 45 min; 95° C. for 2 min; 30 cycles of 95° C. for 15 sec, 68° C. for 1 min, 72° C. for 1 min; 72° C. for 5 min. Negative controls were performed by adding 1° L of RNase (10 mg/mL) and incubating at 37° C. for 1 hr before adding AccessQuick reagents and cycling.

In Situ Hybridization

In situ hybridization was performed as described previously with modifications as described by Root et al. Brain and pituitary were dissected from two parasitic lampreys and were oriented for horizontal sectioning. The GnRH-R probes were produced by reverse transcription of two PCR-amplified (GSP13 vs. GSP8 and GSP19 vs. GSP24) portions of the GnRH receptor transcript using the RIBOPROBE Synthesis System (PROMEGA). These represent a 500-nucleotide sequence that includes the coding sequence from the extracellular end of transmembrane region 1 through the C-terminal end of extracellular loop 1 and a 336-nucleotide sequence corresponding to the coding region of intracellular loop 3 through the middle of the Cterminal tail. A mixture of these two probes was used (10.0 ng/µL of each). Results Lamprey GnRH Receptor cDNA Isolation and Sequencing Using PCR from genomic template with degenerate primers and subsequent 5 RACE from brain cDNA, a 1,838-base full-length cDNA was identified and confirmed with at least three separate clones to each portion of the sequence. This transcript contains a 55-base 5 untranslated region, and a 1,380-base coding region, and a 458-base 3 untranslated region. Translation of the coding region demonstrated that the identified transcript encoded a GnRH receptor sequence of 460 amino acids. Within this open reading frame, all of the regions of a 7TM GPCR were predicted (FIG. 1).

Lamprey GnRH Receptor cDNA Sequence Analysis

The amino acid sequence encoded by the lamprey GnRH receptor transcript has high identity to numerous GnRH receptors previously identified. The receptor amino acid sequence was compared to all previously identified GnRH receptors using MegAlign (LASERGENE). It has highest identity to those of the aquatic caecilian *Typhlonectes natans* (61.2%) (unpublished, GenBank # AF174481), the amphibian *Rana catesbeiana* (receptor 1:60.7% and receptor 2:59.8%), and the striped sea bass *Morone saxitilis* (59.6%). The chicken GnRH receptor and the human GnRH receptor were also used in this analysis and were found to have 43% and 40% identity, respectively (FIG. 2). The lamprey GnRH receptor amino acid sequence was examined for conservation of the characteristic motifs of Class A GPCRs and of GnRH receptors (FIG. 3). The putative lamprey GnRH receptor maintains all of the conserved motifs of Class A GPCRs with the exceptions characteristic of GnRH receptors. Based on this comparison, the lamprey GnRH receptor appears more closely related to type-II GnRH receptors than to type-I GnRH receptors.

Lamprey GnRH Receptor Functional Analysis

Both lamprey GnRH-I and lamprey GnRH-III stimulated a significant response in both IP and cAMP accumulation, in a dose dependant manner, in COS7 cells that were transiently transfected with the lamprey GnRH receptor (FIG. 4). The LogEC50's (represented as mean±SEM; n=3) of lamprey GnRH-III, relative to both IP (−9.37±0.243) and cAMP (−8.29±0.090) were significantly (P<0.0002) lower then the LogEC50's of lamprey GnRH-I (−8.10±0.150 and −6.57±0.150, respectively). This significant difference in activation of both second messenger systems suggests the presently cloned lamprey GnRH-R is lamprey GnRH-III selective. Cells transfected with blank pcDNA3.1 vector showed no response in IP or cAMP accumulation following treatment with ether lamprey GnRH-I or lamprey GnRH-III (data not shown).

Phylogenetic Analysis of GnRH Receptors

Phylogenetic analysis was performed using an alignment (MegAlign, ClustalW) of the predicted lamprey GnRH receptor protein sequence with 36 previously identified GnRH receptor protein sequences (FIG. 5). The GnRH receptors grouped into three phylogenetic clades, with the lamprey receptor grouping with type II GnRH receptors from amphibians and mammals as well as with three fish receptors. The GnRH-like receptors identified from the tunicate form outgroups. Sequences used: mouse, human, rat, sheep, cow, pig, bonnet macaque, rhesus monkey, dog, horse (unpublished, GenBank # AF018072), guinea pig, wallaby, gecko, tunicate, amberjack (unpublished, GenBank # AJ130876), Rio Cauca caecilian (unpublished, GenBank #AF174481), African green monkey, marmoset, chicken, bullfrog, brown frog, African clawed frog, catfish, goldfish, striped sea-bass, rainbow trout, Japanese eel, and Japanese medaka.

Tissue-Specific Expression

The target sequence of approximately 840 bases was visualized in pars intermedia, proximal pars distalis, rostral pars distalis, and testes (FIG. 6) following RT-PCR from lamprey proximal pars distalis, rostral pars distalis, brain, ovary, testes, heart, muscle, liver, kidney, and eye.

Expression appeared high in the proximal pars distalis and testes and low in the rostral pars distalis.

In Situ Hybridization

Expression was visualized by in situ hybridization in the proximal pars distalis of the lamprey pituitary (N=2) (FIG. 7). This expression is seen in the same portion of the lamprey pituitary in which GnRH binding sites are known to be concentrated. GnRH receptor transcript expression was not detected in the lamprey brain. Because of the limited availability of adult lamprey brains and pituitaries, juvenile lampreys were used for this study.

Discussion

A 1,838-base full-length cDNA encoding a putative GnRH receptor has been identified from sea lamprey pituitary. This transcript sequence includes a 55-base 5'-untranslated region; a 1,380-base reading frame, based on translation starting at the first AUG methionine codon, encoding a full seven transmembrane receptor protein of 460 amino acids; and a 403-base 3' untranslated region. Analysis of the encoded amino acid sequence showed maintenance of the characteristic motifs of GnRH receptors and high overall similarity to previously identified GnRH receptors. The lamprey GnRH receptor was shown to be functional by the stimulation of both IPs and cAMP in transiently transfected COS7 cells. Expression of the receptor transcript was demonstrated by RT-PCR in the proximal pars distalis and rostral pars distalis of the pituitary, as well as in the testes. Expression was also visualized in the proximal pars distalis of the juvenile lamprey pituitary by in situ hybridization with digoxigenin-labeled riboprobes. The GnRH receptor family is unique among G protein-coupled receptors because a number of its members lack an intracellular C-terminal tail. All of these tailless receptors have been identified from mammalian species, and since the first six GnRH receptors identified were tailless, it was originally thought that all GnRH receptors lacked a C-terminal tail. In 1997, the first tailed GnRH receptor was identified in the African catfish. The implications of this variation in presence or absence of the C-terminal tail remains an important subject of investigation. Various studies have shown that the C-terminal tail of GPCRs has an important role in controlling expression, membrane cycling, desensitization, and G protein activation. Progressive truncation of the C-terminal tail of the catfish receptor 1 was shown to drastically and progressively reduce surface expression of the receptor, and addition of the catfish GnRH receptor 1 C-terminal tail to the rat GnRH receptor greatly increased the surface expression of the receptor construct. The known tailed receptors contain intracellular tails of varying sizes from 40-80 amino acids in length. The current lamprey GnRH receptor includes a C-terminal tail of 120 amino acids; this is the longest C-terminal end identified to date in a GnRH receptor. These data indicate that the long C-terminal tail of the putative lamprey GnRH receptor may function, in part, to produce the high levels of surface expression demonstrated in our previous GnRH binding studies. Analysis of the lamprey GnRH receptor amino acid sequence revealed that it contains four potential methionine start codons within the first 13 codons of the reading frame (FIG. 1). It is unknown which one of these start codons is used, but multiple start codons are not unusual in GnRH receptor transcripts. The regional comparison of this transcript to other GnRH receptors demonstrates maintenance of the high sequence conservation of the transmembrane helices and of intracellular loop 2. The relatively low conservation of extracellular loop 3, the most crucial region of the receptor for ligand specificity, was also maintained. The variations in the conserved GPCR motifs were also similar to other type-II GnRH receptors identified to date, as was the hydropathy plot of the predicted protein (data not shown). Activation of GnRH receptors is generally known to stimulate the IP3 and/or cAMP second messenger systems, which in turn lead to several downstream responses including the synthesis and secretion of the gonadotropins. However, the exact nature of this signaling and the differences in signaling between the type I and type II GnRH-receptors is not well understood. It has been proposed that GnRH receptors primarily function through the IP3 system, which was primarily based on the analysis of type I receptors. More recently it has been suggested that type I GnRH receptors predominantly function through the IP3 system, while the tailed type II receptors function through both the IP3 and cAMP systems. This is likely due to the structural differences between the two groups (most notably the presence or absence of an intracellular C-terminal tail). Consistent with this latter characterization, stimulation of the cloned type II lamprey GnRH receptor, with either lamprey GnRH-I or lamprey GnRH-III, was shown to activate both the IP and cAMP systems, dose dependently, in transiently transfected COS7 cells. Lamprey GnRH-III was shown to be the most potent of the two forms at stimulating both signaling systems (see FIG. 4) with logEC50's approximately 40-50 fold lower then the logEC50's of lamprey GnRH-I, and therefore may be the native ligand for this cloned receptor. This differential activation correlates well with the previous identification of two high affinity GnRH binding sites in the lamprey pituitary, further supporting the hypothesis that the lamprey express at least two GnRH receptors. RT-PCR indicated expression of the lamprey GnRH receptor transcript in both the pituitary and testes. The receptor transcript was strongly detected in the proximal pars distalis of the pituitary and in the testes. It was also weakly detected in the rostral pars distalis. These data are consistent with GnRH binding studies performed in the sea lamprey. Pituitary and gonadal expression of GnRH receptor transcripts has also been demonstrated in other models, including mammals and teleost fish. In situ hybridization with a specific riboprobe to the lamprey GnRH receptor showed moderate levels of expression in the proximal pars distalis of the pituitary (FIG. 7). This distribution of GnRH receptor expression is similar to the distribution of GnRH binding sites characterized in the sea lamprey pituitary by quantitative in vitro autoradiography. Characterization of GnRH binding sites within the lamprey pituitary at various stages of development has shown a dramatic increase in GnRH receptor expression levels during gonadal maturation. These data showed that the levels of GnRH receptor in the pituitary of sexually mature lamprey are high, reaching a Bmax of 1.0×10 11, compared to the range reported in goldfish, 10-9. A corresponding increase has been shown in lamprey GnRH concentrations as lampreys mature, with a particularly dramatic increase in the level of lamprey GnRH-III preceding ovulation. Pituitary expression and differential activation of the present GnRH receptor strongly indicate that this receptor is a key player in the reproductive development and function of the sea lamprey. The similarity of the lamprey GnRH receptor amino acid sequence to that of other type II GnRH receptors and its close phylogenetic grouping with the recently identified type II mammalian GnRH receptors suggest that this receptor represents an ancestral form of the type II GnRH receptor. The visualization of the lamprey receptor transcript in multiple tissues implies that, like other type II receptors, this receptor may have functions outside the pituitary in addition to binding to GnRH in the pituitary. The phylogenetic relationship of the GnRH receptor family has been described in numerous studies. One classification of GnRH receptors is based on a scheme presented by Troskie, et al. using the amino acids motifs in extracellular loop 3 to group the GnRH receptors using phylogenetic analysis into two main groups, type I and type II. Millar et al. (1) recently provided a new classification of the GnRH receptors (type I, II and III) using phylogenetic analysis based on the amino acid structures of the full-length cloned receptors. Okubo, et al. have presented an additional phylogenetic analysis of a larger groups of GnRH receptors and have used the entire receptor sequence (21). They identified three main groups as well, and suggested grouping of the receptors based on the presence or absence of the C-terminal tail and the intron structure of the GnRH receptor genes (21). Based on the present data, we provide a modification in the classification scheme of GnRH receptors. The phylogenetic analysis, using the full-length GnRH receptor sequences and using virtually all known GnRH receptor sequences, shows three main groupings. These groups agree well with the groups identified by Troskie, et al., and Okubo, et al., in the relative members of each group; however, the present analysis, like that of Okubo, et al., suggests that the two clades that are not exclusively made up of mammalian tailless receptors are more closely related to one another than either is to the mammalian tailless clade. In light of these data, it is shown that, rather than a subdivision among the type I receptors, the subdivision is more appropriately assigned within the type II receptors. In conclusion, a full-length cDNA for a GnRH receptor was identified from the sea lamprey pituitary. The coded amino acid sequence of this transcript was similar to that of known GnRH receptors and maintained the conserved properties of these receptors. Stimulation of the cloned lamprey GnRH receptor led to a dose dependant response in accumulation of both IP and cAMP when treated with either lamprey GnRH-I or lamprey GnRH-III. Expression analysis of this transcript by RT-PCR showed that it is detectable in both the pituitary and testes of adult lampreys. Expression mapping of this transcript using in situ hybridization in the brain and pituitary of the sea lamprey demonstrated that it is expressed primarily in the proximal pars distalis of the lamprey pituitary, in concurrence with GnRH in vitro autoradiography studies in the lamprey pituitary. The current study is the first to identify a pituitary GnRH receptor transcript in an agnathan. The phylogenetic placement and structural features of this GnRH receptor suggest that it is representative of an ancestral type II GnRH receptor. In addition to having an important role in lamprey reproductive processes, the extensive C-terminal tail of this lamprey GnRH receptor has great significance for understanding the evolutionary change of this vital structural feature within the GnRH receptor family.

While examples have been given, the present invention is not to be limited in scope by the exemplified embodiments shown herein, which are intended only as illustrations of single aspects of the invention. Any clones, DNA or amino acid sequences that are functionally equivalent, including analogs, to any examples herein are within the scope of the invention. It should also be understood that all base pair sizes given for nucleotides are approximate and are used for purposes of description only. Various modifications of the invention are possible, in addition to those provided in the foregoing description and accompanying drawings, and such modifications are intended to fall within the scope of invention as well.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention, which is not to be limited except by the following claims.

The invention claimed is:

1. An isolated and purified DNA selected from the group consisting of SEQ ID NO: 1 and any nucleotide sequence coding for the GnRH recepter protein comprising the amino acid sequence of SEQ ID NO:2.

2. A vector comprising said DNA of claim 1.

3. A transformant comprising said vector of claim 2.

4. A process for producing a GnRH receptor protein or a salt thereof comprising culturing said transformant of claim 3 under sufficient conditions and for appropriate time to express said GnRH receptor protein.

5. The process of claim 4, further comprising allowing said GnRH receptor protein or salt thereof to accumulate, and collecting said GnRH receptor protein or a salt thereof.

6. An isolated and purified DNA of claim 1 comprising the nucleotide sequence from nucleotide 54 to nucleotide 1434 of SEQ ID NO: 1.

* * * * *